United States Patent [19]

Arnould

[11] Patent Number: 5,607,928
[45] Date of Patent: Mar. 4, 1997

[54] CARBAPENEM DERIVATIVES CONTAINING A BICYCLIC KETONE SUBSTITUENT AND THEIR USE AS ANTI-INFECTIVES

[75] Inventor: Jean-Claude Arnould, Cormontreuil, France

[73] Assignees: Zeneca Limited, London, England; Zeneca Pharma SA, Cergy Cedex, France

[21] Appl. No.: 508,698

[22] Filed: Jul. 28, 1995

[30] Foreign Application Priority Data

Aug. 5, 1994 [EP]  European Pat. Off. ............ 944018142

[51] Int. Cl.$^6$ .................... C07D 487/04; A61K 31/40
[52] U.S. Cl. ........................................... 514/210; 540/302
[58] Field of Search ............................ 540/302; 514/210

[56] References Cited

U.S. PATENT DOCUMENTS 5,068,232  11/1991  Ziegler, Jr. et al. .

FOREIGN PATENT DOCUMENTS

| | | |
|---|---|---|
| 0010316 | 4/1980 | European Pat. Off. . |
| 0184844 | 6/1986 | European Pat. Off. . |
| 0184842 | 6/1986 | European Pat. Off. . |
| 0186057 | 7/1986 | European Pat. Off. . |
| 0292191 | 11/1988 | European Pat. Off. . |
| 0336143 | 10/1989 | European Pat. Off. . |
| 0366189 | 5/1990 | European Pat. Off. . |
| 0451764 | 10/1991 | European Pat. Off. . |
| 58-103388 | 6/1983 | Japan . |
| 59-36677 | 2/1984 | Japan . |
| 59-33285 | 2/1984 | Japan . |
| 1-93586 | 4/1989 | Japan . |
| 1-279888 | 11/1989 | Japan . |
| 2092147 | 8/1982 | United Kingdom . |
| 93/07154 | 4/1993 | WIPO . |

OTHER PUBLICATIONS

Corraz et al.; Duel–Action Penems and Carbapenems; J. Med. Chem.; 1992, pp. 1828–1839.

Primary Examiner—Rebecca Cook
Attorney, Agent, or Firm—Cushman Darby & Cushman Intellectual Property Group of Pillsbury Madison & Sutro LLP

[57] ABSTRACT

The present invention relates to carbapenems and provides a compound of the formula (I)

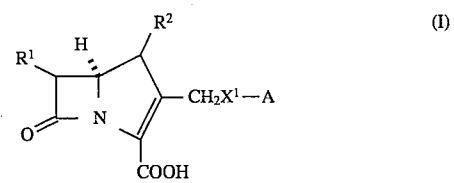

wherein
  $R^1$ is hydroxymethyl, 1-hydroxyethyl or 1-fluoroethyl;
  $R^2$ is hydrogen or $C_{1-4}$alkyl;
  $X^1$ is oxygen or sulphur; and
  A is of the formula

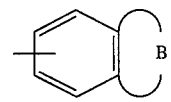

which is optionally substituted on either ring and wherein B is of the formula —$CH_2$—$C(=O)$—$(CH_2)_n$—, —$C(=O)$—$(CH_2)_{n1}$—, —$C(=O)$—$CH=CH$—$X^2$—, —$C(=O)CH_2CH_2X^2$—, —$(CH_2)_nC(=O)NH$— or —$CH=CHC(=O)NH$— wherein n is 1 or 2, $n^1$ is 2 or 3 and $X^2$ is NH, O or S;

and a pharmaceutically acceptable salt or an in vivo hydrolysable ester thereof, processes for their preparation, intermediates in their preparation, their use as therapeutic agents and pharmaceutical compositions containing them.

16 Claims, No Drawings

CARBAPENEM DERIVATIVES CONTAINING A BICYCLIC KETONE SUBSTITUENT AND THEIR USE AS ANTI-INFECTIVES

The present invention relates to antibiotic compounds and in particular to carbapenem antibiotics containing a bicyclic ketone. This invention further relates to processes for their preparation, to intermediates useful in their preparation, to their use as therapeutic agents and to pharmaceutical compositions containing them.

The international microbiological community continues to express serious concern that the evolution of antibiotic resistance could result in strains against which currently available antibacterial agents will be ineffective. In general, bacterial pathogens may be classified as either Gram-positive or Gram-negative pathogens. Antibiotic compounds with effective activity against both Gram-positive and Gram-negative pathogens are generally regarded as having a broad spectrum of activity. The compounds of the present invention are regarded primarily as effective against Gram-positive pathogens because of their particularly good activity against such pathogens.

Gram-positive pathogens, for example Staphylococci, Enterococci and Streptococci, are particularly important because of the development of resistant strains which are both difficult to treat and difficult to eradicate from the hospital environment once established. Examples of such strains are methicillin resistant staphylococcus (MRSA), methicillin resistant coagulase negative staphylococci (MRCNS), penicillin resistant streptococcus pneumoniae and multiply resistant enterococcus faecium.

The major clinically effective antibiotic for treatment of such resistant Gram-positive pathogens is vancomycin. Vancomycin is a glycopeptide and is associated with nephrotoxicity and ototoxicity. Furthermore, and most importantly, antibacterial resistance to vancomycin and other glycopeptides is also appearing. This resistance is increasing at a steady rate rendering these agents less and less effective in the treatment of Gram-positive pathogens.

The present inventors have discovered a narrow class of carbapenem compounds containing a bicyclic ketone which have useful activity against Gram-positive pathogens including MRSA and MRCNS and, in particular, against various strains exhibiting resistance to vancomycin and against E. faecium strains resistant to both aminoglycosides and clinically used β-lactams.

Substantial investigations have been made into carbapenem antibiotics over the past two decades and, to date, two carbapenems, imipenem and panipenem have been marketed:

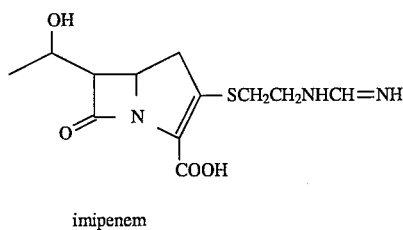

imipenem

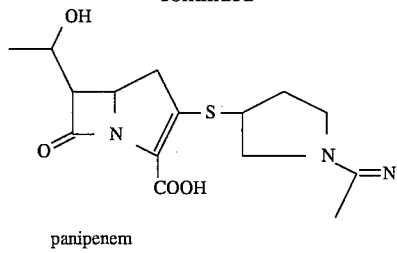

panipenem

Both of these carbapenem compounds are regarded as broad spectrum agents.

The carbapenem derivatives referred to herein are named in accordance with the generally accepted semi-systematic nomenclature:

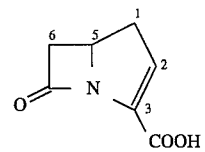

EP-A-184844 and 186057 disclose a broad range of carbapenem compounds having a 2-position substituent of the formula —$R^4$—X—$R^5$ wherein $R^4$ is various linking groups including $C_{2-4}$alkyl, X is —S—, —SO—, —$SO_2$, —O— or —NH— and $R_5$ is an unsubstituted or substituted aliphatic radical which can include heterocyclic and heteroarylium substituents. $R^5$ is defined more specifically to include substituted phenyl and mono or bicyclic heterocyclic groups. These compounds are described as broad spectrum antibacterial agents.

$\Delta^2$—Endo—, $\Delta^1$—endo, and exo carbapenem compounds having a 2-position substituent of the formula -CHXY, wherein X is fluoro, chloro, bromo, iodo or hydrogen and Y can be one of a variety of —C(=O)R or —C(=S)R groups or $SR^{17}$, $SOR^{17}$, $SO_2R^{17}$, fluoro, chloro, bromo or iodo, are disclosed in U.S. Pat. No. 5,068,232. In this patent $R^{17}$ can be an optionally substited phenyl ring or a fused phenyl ring, optionally a phenyl ring fused to a 5- or 6- membered heteroaryl ring. The compounds are disclosed generally as antibiotics and β-lactamase inhibitors.

There is no suggestion that the compounds of EP-A-184, 844, EP-A-186,057 or U.S. Pat. No. 5,068,232 possess particularly beneficial activity against resistant Gram-positive pathogens as described hereinabove.

We have now discovered a narrow class of compounds that is not suggested by the art and which has good activity against a broad range of Gram-positive pathogens including organisms known to be resistant to most commonly used antibiotics.

Accordingly the present invention provides a compound of the formula (I)

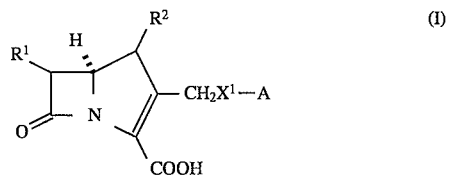

wherein
$R^1$ is hydroxymethyl, 1-hydroxyethyl or 1-fluoroethyl;
$R^2$ is hydrogen or $C_{1-4}$alkyl;
$X^1$ is oxygen or sulphur; and A is of the formula

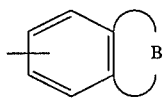

which is optionally substituted on either ring and wherein B is of the formula —$CH_2$—C(=O)—$(CH_2)_n$—, —C(=O)—$(CH_2)_{n1}$—, —C(=O)—CH=CH—$X^2$—, —C(=O)$CH_2CH_2X^2$—, —$(CH_2)_n$C(=O)NH— or —CH=CHC(=O)NH— wherein n is 1 or 2, $n^1$ is 2 or 3 and $X^2$ is NH, O or S; and a pharmaceutically acceptable salt or an in vivo hydrolysable ester thereof.

Preferably $R^1$ is 1-hydroxyethyl.
Preferably $R^2$ is hydrogen or methyl.
More preferably $R^2$ is methyl.
Preferably $X^2$ is O or S.
Preferably, B is of the formula —C(=O)$CH_2CH_2$—, —C(=O)$CH_2CH_2CH_2$—, —C(=O)CH=CH—O—, —C(=O)$CH_2CH_2$O—, —NHC(=O)$CH_2$—, —NHC(=O)$CH_2CH_2$— or —C(=O)$CH_2CH_2$S—.
Preferably A is substituted by 0 1 or 2 substituents.

Suitable optional substituents for ring carbon atoms in A include those substituents in lists a) and b):

a) $C_{1-4}$alkanoyl for example acetyl or propionyl;
hydroxy $C_{1-2}$alkyl for example hydroxymethyl or hydroxyethyl;
cyano;
carbamoyl;
$C_{1-4}$alkylcarbamoyl for example methylcarbamoyl or ethylcarbamoyl;
di-$C_{1-4}$alkylcarbamoyl for example dimethylcarbamoyl or diethylcarbamoyl;
$C_{1-4}$alkyls(O)$_p$—wherein p is 1 or 2 for example
methylsulphonyl or methylsulphinyl;
aminosulphonyl;
$C_{1-4}$alkylaminosulphonyl for example methylaminosulphonyl;
di-$C_{1-4}$alkylaminosulphonyl for example dimethylaminosulphonyl;
amino$C_{1-2}$alkyl for example aminomethyl or aminoethyl;
$C_{1-4}$alkylamino$C_{1-2}$alkyl for example methylaminomethyl;
di-$C_{1-4}$alkylamino$C_{1-2}$alkyl for example dimethylaminomethyl or dimethylaminoethyl;
hydroxyiminomethyl;
$C_{1-4}$alkoxyiminomethyl for example methoxyiminomethyl;
$C_{1-4}$alkanesulphonamido for example methanesulphonamido;
(N-$C_{1-4}$alkyl)—$C_{1-4}$alkanesulphonamido for example (N-methyl)methane sulphonamido; or
$C_{1-2}$alkyl substituted by any one of tri-$C_{1-4}$alkylammonium, N-$C_{1-4}$ alkylimidazolium, N-imidazole or N-pyridinium (optionally substituted on a ring carbon by amino) (the pyridinium, imidazolium and imidazole rings being linked via a ring nitrogen), for example pyridiniummethyl, N-methylimidazoliummethyl and imidazolemethyl;
$C_{1-4}$alkylamino for example methylamino and ethylamino;
di-$C_{1-4}$alkylamino for example dimethylamino and diethylamino;
$C_{1-4}$alkanoylamino for example acetamido;
thienyl$C_{1-2}$alkylene for example thienylmethylene;
b) $C_{1-4}$alkylthio for example methylthio;
$C_{1-4}$alkyl for example methyl and ethyl;
amino;
benzoyl;
benzoyl$C_{1-2}$alkyl for example benzoylmethyl;
2-oxo$C_{3-4}$alkyl for example 2-oxo-butyl;
phenylamino$C_{1-2}$alkyl for example phenylaminomethyl;
morpholino; pyridyl$C_{1-2}$alkylene for example pyridylmethylene
halo for example bromo, chloro and fluoro;
nitro;
hydroxy;
$C_{1-4}$alkoxy for example methoxy and ethoxy;
$C_{1-4}$alkoxycarbonyl for example methoxycarbonyl;
carboxy;
sulphonic acid; and
trifluoromethyl.
Preferably A is substituted, (on ring carbon atoms), by one substituent selected from list a) above and is further optionally substituted by a substituent selected from list b) above. Preferably the substituent from list b) is methyl.

In a particular aspect A is mono-substituted on a ring carbon atom by one substituent selected from list a) above.

In another aspect A is mono-substituted on a ring carbon atom by one substituent selected from list b) above.

Particularly preferred substituents are hydroxymethyl, carbamoyl, N-$C_{1-4}$alkylimidazoliummethyl, thienylmethylene, dimethylaminomethyl and dimethylamino.

In particular A is substituted on a ring carbon atom by hydroxymethyl or carbamoyl.

In another aspect ring carbon atoms in A are unsubstituted. Suitable optional substituents for ring nitrogen atoms in A include those substituents in lists $a^1$) and $b^1$):

$a^1$) bromo$C_{1-4}$alkyl for example bromomethyl and bromoethyl;
hydroxy$C_{1-4}$alkyl for example hydroxymethyl and hydroxyethyl;
cyano$C_{1-4}$alkyl for example cyanomethyl and cyanoethyl;
carbamoyl$C_{1-4}$alkyl for example carbamoylmethyl and carbamoylethyl;
$R^a(CH_2)n''$, wherein Ra is a 5- or 6- membered heteroaryl ring having one or two ring nitrogens as the heteroatoms wherein one ring nitrogen is optionally quaternised and n'' is 1-4, for example pyridiniummethyl, methylimidazoliummethyl, pyridylmethyl and imidazolylmethyl;
$R^bS(CH2)n''$- wherein n'' is as hereinabove defined and $R^b$ is $C_{1-4}$alkyl or a 5- or 6- membered heteroaryl ring having one or two ring nitrogens as the heteroatoms, for example, methylthiomethyl, ethylthiomethyl, pyridylthiomethyl, pyrimidylthiomethyl and imidazolylthiomethyl, and $b^1$) $C_{1-4}$alkyl for example methyl, ethyl and propyl;
$C_{1-4}$alkenyl for example allyl and 3-butenyl;
$C_{1-4}$alkanoyl for example acetyl and propionyl;
benzoyl; and
pyridoyl;

wherein any phenyl or heteroaryl group in a substituent on a ring nitrogen atom in A may be optionally substituted. Examples of suitable substituents for such groups include hydroxy, halo, $C_{1-4}$alkyl, nitro, amino, carbamoyl, cyano and trifluoromethyl.

Preferably a ring nitrogen in A is unsubstituted or substituted by a substituent from list a$^1$).

In another aspect a ring nitrogen in A is unsubstituted or substituted by methyl.

Optional substituents on A may be situated on either ring. Thus the benzene part of A, or the unsaturated part of A or both of these rings simultaneouly may be substituted.

Preferably A is substituted on B.

The term 'alkyl' includes both straight and branched chains for example $C_{1-4}$alkyl includes ethyl, n-propyl and isopropyl. This convention also extends to other radicals.

The present invention covers all epimeric, diastereoisomeric and tautomeric forms of the compounds of the formula (I) wherein the absolute stereochemistry at the 5-position is as illustrated in formula (I). The compounds of the formula (I) have a number of other stereocentres, namely: within the group $R^2$ (when $R^2$ is 1-fluoroethyl or 1-hydroxyethyl); and at the 6-position, at the 1-position when $R^1$ is $C_{1-4}$ alkyl.

Preferred compounds are those in which the beta-lactam ring protons are in trans configuration with respect to one another. When $R^2$ is 1-fluoroethyl or 1-hydroxyethyl it is preferred that the configuration is R and when $R^1$ is $C_{1-4}$alkyl for example methyl it is preferred that the compound is in the form of the 1S configuration.

Thus a preferred class of compounds is that of the formula (II):

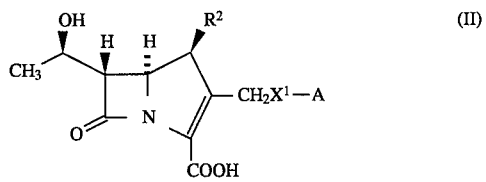

wherein $R^2$, $X^1$ and A are as hereinbefore defined and A is optionally substituted and pharmaceutically acceptable salts and in vivo hydrolysable esters thereof.

Suitable pharmaceutically acceptable salts include acid addition salts such as hydrochloride, hydrobromide, citrate, maleate and salts formed with phosphoric and sulphuric acid. In another aspect suitable salts are base salts such as an alkali metal salt for example sodium or potassium, an alkaline earth metal for example calcium or magnesium, an organic amine salt for example triethylamine, morpholine, N-methylpiperidine, N-ethylpiperidine, procaine, dibenzylamine, N,N-dibenzylethylamine or amino acids for example lysine.

Preferred pharmaceutically acceptable salts are sodium and lysine salts most preferably sodium salts. However, to facilitate isolation of the salt during preparation, salts which are less soluble in the chosen solvent may be preferred whether pharmaceutically acceptable or not.

In vivo hydrolysable esters are those pharmaceutically acceptable esters that hydrolyse in the human body to produce the parent compound. Such esters can be identified by administering, eg. intravenously to a test animal, the compound under test and subsequently examining the test animal's body fluids. Suitable in vivo hydrolysable esters for carboxy include $C_{1-6}$alkoxymethyl esters for example methoxymethyl, $C_{1-6}$alkanoyloxymethyl ester for example pivaloyloxymethyl, phthalidyl esters, $C_{3-8}$cycloalkoxycarbonyloxy- $C_{1-6}$alkyl esters for example 1-cyclohexyloxycarbonyloxyethyl; 1,3-dioxolen-2-onylmethyl esters for example 5-methyl-1,3-dioxolen-2-onylmethyl; and $C_{1-6}$alkoxycarbonyloxyethyl esters for example 1-methoxycarbonyloxyethyl and may be formed at any carboxy group in the compounds of this invention. Suitable in vivo hydrolysable ester forming groups for hydroxy include acetyl, propionyl, pivaloyl, $C_{1-4}$alkoxycarbonyl for example ethoxycarbonyl and phenylacetyl.

In order to use a compound of the formula (I) or a pharmaceutically acceptable salt or in vivo hydrolysable ester thereof for the therapeutic treatment of mammals including humans, in particular in treating infection, it is normally formulated in accordance with standard pharmaceutical practice as a pharmaceutical composition.

Therefore in another aspect the present invention provides a pharmaceutical composition which comprises a compound of the formula (I) or a pharmaceutically acceptable salt or in vivo hydrolysable ester thereof and a pharmaceutically acceptable carrier.

The pharmaceutical compositions of this invention may be administered in standard manner for the disease condition that it is desired to treat, for example by oral, rectal or parenteral administration. For these purposes the compounds of this invention may be formulated by means known in the art into the form of, for example, tablets, capsules, aqueous or oily solutions or suspensions, emulsions, dispersible powders, suppositories and sterile injectable aqueous or oily solutions or suspensions.

The compounds of the present invention may be formulated as dry powder filled vials, which may contain the compound of the present invention alone or as a dry blended mixture. For example an acidic compound of the present invention may be dry blended with an alkali metal carbonate or bicarbonate. Freeze dried formulations of compounds of the present invention, alone or as a mixture with standard excipients, are possible. Standard excipients include structure formers, cryoprotectants and pH modifiers, such as, mannitol, sorbitol, lactose, glucose, sodium chloride, dextran, sucrose, maltose, gelatin, bovine serum albumin (BSA), glycine, mannose, ribose, polyvinylpyrrolidine (PVP), cellulose derivatives, glutamine, inositol, potassium glutamate, erythritol, serine and other amino acids and buffer agents e.g. disodium hydrogen phosphate and potassium citrate.

In addition to the compounds of the present invention the pharmaceutical composition of this invention may also contain, or be co-administered with, one or more known drugs selected from other clinically useful antibacterial agents (for example other beta-lactams or aminoglycosides), inhibitors of beta-lactamase (for example clavulanic acid), renal tubular blocking agents (e.g. probenecid) and inhibitors of metabolising enzymes (for example inhibitors of dehydropeptidases, for example Z-2-acylamino-3-substituted propenoates such as cilastatin) and N-acylated amino acids (for example see EP-A-178911) which reduce adverse effects on the kidney.

A suitable pharmaceutical composition of this invention is one suitable for oral administration in unit dosage form, for example a tablet or capsule which contains between 100 mg and 1 g of the compound of this invention.

A preferred pharmaceutical composition of the invention is one suitable for intravenous, subcutaneous or intramuscular injection, for example a sterile injectable containing between 1 and 50% w/w of the compound of this invention.

The pharmaceutical compositions of the invention will normally be administered to man in order to combat infections caused by bacteria, in the same general manner as that employed for imipenem due allowance being made in terms of dose levels for the potency and duration of action of the compound of the present invention relative to the clinical use of imipenem. Thus for example each patient may receive a daily intravenous, subcutaneous or intramuscular dose of 0.05 to 5 g and preferably 0.1 to 2.5 g of the compound of this invention, the composition being administered 1 to 4 times per day. The intravenous, subcutaneous and intramuscular dose may be given by means of a bolus injection. Alternatively the intravenous dose may be given by continuous infusion over a period of time. Alternatively each patient will receive a daily oral dose which is approximately equivalent to the daily parenteral dose. Thus a suitable daily oral dose is 0.05 to 5 g of the compound of this invention, the composition being administered 1 to 4 times per day.

In a further aspect the present invention provides a process for preparing a compound of the formula (I) or a pharmaceutically acceptable salt or in vivo hydrolysable ester thereof which process comprises deprotecting a compound of the formula (III):

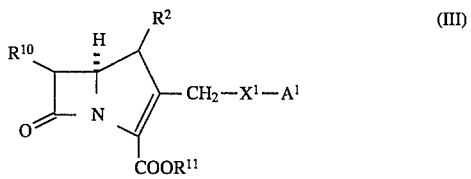

wherein $R^2$ and $X^1$ are as hereinbefore defined and $R^{10}$ is a group $R^1$, protected 1-hydroxyethyl or protected hydroxymethyl, $COOR^{11}$ is carboxy or protected carboxy and $A^1$ is A in which any substituents are optionally protected if appropriate; and wherein at least one protecting group is present; and thereafter if necessary:

i) forming a pharmaceutically acceptable salt;

ii) forming an in vivo hydrolysable ester.

Protecting groups may in general be chosen from any of the groups described in the literature or known to the skilled chemist as appropriate for the protection of the group in question, and may be introduced by conventional methods.

Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

The compounds of the formula (III) are novel and form another aspect of the invention.

Specific examples of protecting groups are given below for the sake of convenience, in which "lower" signifies that the group to which it is applied preferably has 1–4 carbon atoms. It will be understood that these examples are not exhaustive. Where specific examples of methods for the removal of protecting groups are given below these are similarly not exhaustive. The use of protecting groups and methods of deprotection not specifically mentioned is of course within the scope of the invention.

A carboxyl protecting group may be the residue of an ester-forming aliphatic or araliphatic alcohol or of an ester-forming silanol (the said alcohol or silanol preferably containing 1–20 carbon atoms).

Examples of carboxy protecting groups include straight or branched chain (1–12C)alkyl groups (eg isopropyl, t-butyl); lower alkoxy lower alkyl groups (eg methoxymethyl, ethoxymethyl, isobutoxymethyl; lower aliphatic acyloxy lower alkyl groups, (eg acetoxymethyl, propionyloxymethyl, butyryloxymethyl, pivaloyloxymethyl); lower alkoxycarbonyloxy lower alkyl groups (eg 1-methoxycarbonyloxyethyl, 1-ethoxycarbonyloxyethyl); aryl lower alkyl groups (eg p-methoxybenzyl, o-nitrobenzyl, p-nitrobenzyl, benzhydryl and phthalidyl); tri(lower alkyl)silyl groups (eg trimethylsilyl and t-butyldimethylsilyl); tri(lower alkyl)silyl lower alkyl groups (eg trimethylsilylethyl); and (2–6C)alkenyl groups (eg allyl and vinylethyl).

Methods particularly appropriate for the removal of carboxyl protecting groups include for example acid-, metal- or enzymically-catalysed hydrolysis.

Examples of hydroxyl protecting groups include lower alkenyl groups (eg allyl); lower alkanoyl groups (eg acetyl); lower alkoxycarbonyl groups (eg t-butoxycarbonyl); lower alkenyloxycarbonyl groups (eg allyloxycarbonyl); aryl lower alkoxycarbonyl groups (eg benzoyloxycarbonyl, p-methoxybenzyloxycarbonyl, o-nitrobenzyloxycarbonyl, p-nitrobenzyloxycarbonyl); tri lower alkyl/arylsilyl groups (eg trimethylsilyl, t-butyldimethylsilyl, t-butyldiphenylsilyl); aryl lower alkyl groups (eg benzyl) groups; and triaryl lower alkyl groups (eg triphenylmethyl).

Examples of amino protecting groups include formyl, aralkyl groups (eg benzyl and substituted benzyl, eg p-methoxybenzyl, nitrobenzyl and 2,4-dimethoxybenzyl, and triphenylmethyl); di-p-anisylmethyl and furylmethyl groups; lower alkoxycarbonyl (eg t-butoxycarbonyl); lower alkenyloxycarbonyl (eg allyloxycarbonyl); aryl lower alkoxycarbonyl groups (eg benzyloxycarbonyl, p-methoxybenzyloxycarbonyl, o-nitrobenzyloxycarbonyl, p-nitrobenzyloxycarbonyl; trialkylsilyl (eg trimethylsilyl and t-butyldimethylsilyl); alkylidene (eg methylidene); benzylidene and substituted benzylidene groups.

Methods appropriate for removal of hydroxy and amino protecting groups include, for example, acid-, metal- or enzymically-catalysed hydrolysis, for groups such as p-nitrobenzyloxycarbonyl, photolytically and for groups such as silyl groups, fluoride.

Preferred protecting groups for carboxy in compounds of the formula (III) are the groups allyl, p-methoxybenzyl and p-nitrobenzyl. A preferred method for removal of the allyl group is by palladium catalysis using tetrakis (triphenylphosphine) palladium in a dipolar aprotic solvent mixture, such as dichloromethane/ethyl acetate. A sodium salt such as sodium 2-ethylhexanoate may be present to allow isolation of the product by precipitation of the sodium salt.

Preferred methods for removal of the p-nitrobenzyl group are hydrogenation using a palladium catalyst or zinc in an acidic medium.

A preferred method of removal of the p-methoxybenzyl group is with aluminium chloride ($AlCl_3$) in a mixture of dichloromethane/anisole.

Preferred protecting groups for hydroxy are allyloxycarbonyl, 4-nitrobenzyloxycarbonyl and silyl protecting groups such as t-butyldimethylsilyl.

In another aspect of the present invention the compounds of the formulae (I) and (III) may be prepared by a) reacting compounds of the formulae (IV) and (V):

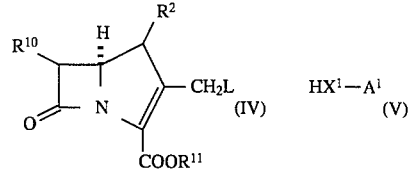

wherein $R^2$, $R^{10}$, $R^{11}$, $X^1$ and $A^1$ are as hereinbefore defined and L is a leaving group, or b) cyclising a compound of the formula (VI):

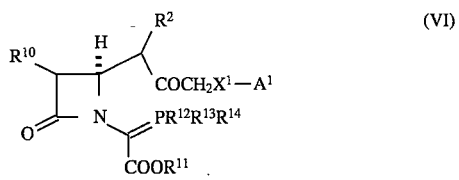

wherein $R^2$, $R^{10}$, $R^{11}$, $X^1$ are $A^1$ are as hereinbefore defined and $R^{12}$—$R^{14}$ are independently selected from $C_{1-6}$alkoxy, aryloxy, di-$C_{1-6}$alkylamino and diarylamino or any two of $R^{12}$—$R^{14}$ represent o-phenylenedioxy; or one of $R^{12}$—$R^{14}$ is $C_{1-4}$alkyl, allyl, benzyl or phenyl, and the other two values are independently selected from $C_{1-4}$alkyl, trifluoromethyl or phenyl, wherein any phenyl group is optionally substituted with $C_{1-3}$alkyl or $C_{1-3}$alkoxy: and wherein any functional group is optionally protected and thereinafter if necessary:

(i) removing any protecting groups;

(ii) forming a pharmaceutically acceptable salt;

(iii) esterifying to form an in vivo hydrolysable ester.

Suitably, in the compounds of the formula (IV), L is a hydroxy group or a reactive ester of a hydroxy group such as a sulphonate (for example $C_{1-6}$alkanesulphonyloxy, trifluoromethanesulphonyloxy, benzenesulphonyloxy or toluenesulphonyloxy). Additionally, when $X^1$ is sulphur, L is halo (for example iodo). Preferably L is hydroxy.

Compounds of the formula (IV) and their preparation are known in the carbapenem literature, for example, they may be prepared by the method or similar methods to that described in the Examples or in EP-A-292191.

The reaction between the compounds of the formulae (IV) and (V) is typically performed under mild neutral conditions, for example as described for the use of the Mitsunobu reaction (Mitsunobu, O. Synthesis, 1981, 1).

Suitably the Mitsunobu reaction is performed in an anhydrous solvent such as dichloromethane, toluene or THF, at ambient temperature and in the presence of di($C_{1-4}$alkyl)azodicarboxylate (for example diisopropylazodicarboxylate and diethylazodicarboxylate) and triphenylphosphine or 1',1'-(azodicarbonyl)dipiperidine (ADDP) and tributylphosphine (Tet. Lett., 34, 1993, 1639–1642). Preferably, when $X^1$ is sulphur, ADDP and tributylphosphine are used.

The compounds of the formula (V) are either commercially available or prepared by standard methods known to the skilled chemist such as the methods of the Examples hereinafter or by methods analogous or similar thereto. More detailed information on the preparation of thiol compounds is given in 'The Chemistry of the thiol group', Parts 1 and 2, edited by Saul Patai (John Wiley & Sons). For example a bromo group can be converted by a thiol group by reacting with NaSH in N-methylpyrrolidone or with butyl lithium followed by dimethylsulphide and demethylation with sodium methanethiolate (Testaferri et al., Tetrahedron Letters (1980), 21, 3099 and Synthesis (1983), 751). More generally halo compounds such as chloro and bromo compounds can be converted to thiols by reacting with potassium tri(isopropyl)silylsulphide in the presence of palladium followed by treatment with potassium fluoride (Tetrahedron Letters, (1994), 35, 3224).

In a further alternative, a hydroxy group can be converted to a thiol group by reacting with a N,N-dimethylthiocarbamoyl chloride in an inert solvent such as dimethylformamide in the presence of a weak base such as potassium carbonate to form the dimethyl thiocarbamic acid 0-ester which isomerises on heating to the dimethyl thiocarbamic acid S-ester which can be converted to the thiol using a strong base such as sodium hydroxide in a protonic solvent such as methanol. (Newman et al., J.O.C. (1966) 31, 3980 and Mayer et al., Tetrahedron Letters (1994) 35, 2161).

Suitably, in the compounds of the formula (VI), $R^{12}$—$R^{14}$ are independently selected from $C_{1-6}$ alkoxy such as methoxy, ethoxy, isopropoxy, n-propoxy or n-butoxy; aryloxy such as optionally substituted phenoxy; aryl such as phenyl, di-$C_{1-6}$alkylamino such as dimethylamino or diethylamino; diarylamino such as diphenylamino or any two of $R^{12}$—$R^{14}$ represent o-phenylenedioxy. Preferably each of $R^{12}$—$R^{14}$ have the same value and are phenyl.

The compounds of the formula (VI) are cyclized under conventional conditions known in the art to form compounds of the formula (II). Typical conditions are heating in a substantially inert organic solvent such as toluene, xylene or ethyl acetate at temperatures in the region 60°–150° C. Typically the reaction is performed in an atmosphere of nitrogen.

The compounds of the formula (VI) may be conveniently prepared by reacting together compounds of the formulae (V) and (VII)

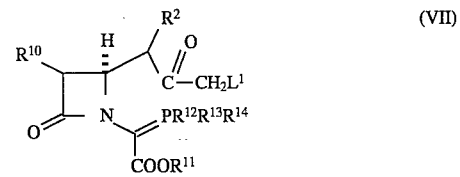

wherein $R^2$ and $R^{10}$—$R^{14}$ are as hereinabove defined and $L^1$ is a leaving group.

Suitably, in the compound of the formula (VII), $L^1$ is a hydroxy group of the reactive ester of a hydroxy group such as those defined for L in the formula (IV). Preferably $L^1$ is mesylate.

The reaction between the compounds of the formulae (V) and (VII) is conveniently performed in an organic solvent such as dichloromethane or DMF in the presence of a base such as N-ethyldiisopropylamine, and in a temperature range of −70° C. to −40° C.

The compounds of the formula (VII) wherein $L^1$ is hydroxy are known in the art. They are typically prepared from a compound of the formula (VIII):

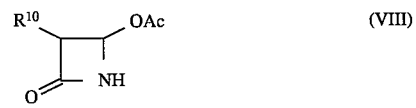

by, for example, using the method or similar methods to that described in EP-A-336,143.

Compounds of the formulae (VI) are novel and, as such, form another aspect of this invention.

The following biological test methods and examples serve to illustrate the present invention.

Antibacterial Activity

The pharmaceutically acceptable carbapenem compounds of the present invention are useful antibacterial agents having a good spectrum of activity in vitro against standard Gram-positive organisms, which are used to screen for activity against pathogenic bacteria. Notably, the pharmaceutically acceptable carbapenem compounds of the present invention show activity against enterococci, pneumococci and methicillin resistant strains of S. aureus and coagulase negative staphylococci. The antibacterial spectrum and potency of a particular compound may be determined in a standard test system.

The antibacterial properties of the compounds of the invention may also be demonstrated in vivo in conventional tests.

Carbapenem compounds have generally been found to be relatively non-toxic to warm-blooded animals, and this generalisation holds true for the compounds of the present invention.

MIC (minimum inhibitory concentration) data were obtained for representative compounds on standard in vitro test systems using Mueller Hinton (MH) agar.

Staphylococci were tested on MH agar, an inoculum of $10^5$ cfu/spot and an incubation temperature of 30° C. for 48 hours—standard test conditions for the expression of methicillin resistance.

Streptococci and enterococci were tested on MH agar supplemented with 5% defibrinated horse blood, an inoculum of $10^4$ cfu/spot and an incubation temperature of 37° C. in an atmosphere of 5% carbon dioxide for 48 hours—blood is required for the growth of some of the test organisms.

The invention will now be illustrated by the following examples in which:

a) nmr spectra were recorded at 400 MHz unless otherwise stated and data are given in δ(ppm);
b) DMF is dimethylformamide:
c) THF is tetrahydrofuran;
d) $CH_3CN$ is acetonitrile;
e) TFA is trifluoroacetic acid:
f) DEAD is diethyl azodicarboxylate
g) ADDP is 1',1'-(azodicarbonyl)dipiperidine
h) DIAD is diisopropyl diazodicarboxylate

EXAMPLE 1

(1S,5R,6S,8R)-6-(1-Hydroxyethyl)-1-methyl-2-(1-tetralone-5-yloxymethyl)carbapenem-3-carboxylic acid sodium salt To a solution of allyl (1S,5R,6S,8R)-6-(1-hydroxyethyl)-1-methyl-2-tetralone-5-yloxymethyl)carbapenem-3-carboxylate (111 mg; 0.26 mmol) in a mixture of $CH_2Cl_2$ (3 ml) and AcOEt (3 ml) was added under argon atomosphere, triphenylphosphine (20 mg; 0.078 mmol), sodium 2-ethylhexanoate (1.24 ml of a 0.22 molar solution in AcOEt; 0.27 mmol) and tetrakis(triphenylphosphine) palladium (30 mg; 0.026 mmol). After stirring for 20 minutes; the solvent was evaporated and the residue triturated in ether. The resulting solid was redissolved in water and purified on reverse phase silica (Nucleosil 120 C18 10 µM) using a gradient of acetonitrile in water (10–15) to give after freeze drying the title compound as a foam (58 mg, 54%).

$^1$H-NMR: (DMSO-$d_6$–ACOD) δ1.12–1.16 (m, 6H); 2.05(t, 2H); 2.55–2.61 (m, 2H); 2.9(t, 2H); 3.2–3.3 (m, 2H); 3.91–3.98(m, 1H); 4.08(dd, 1H), 4.8(d, 1H); 5.48(d, 1H); 7.2(d, 1H); 7.25–7.31 (m, 1H); 7.49 (d, 1H).

MS (+ve) FAB: 408 (MNa+).

The starting material was prepared as follows:

To a solution of allyl (1S,5R,6S,8R)-6-(1-hydroxy-ethyl)-2-hydroxymethyl-1-methylcarbapenem-3-carboxylate [made by heating a solution of (3S,4R, 1'R,1"R)-1-(allyloxycarbonyltriphenyl-phosphoranylidenemethyl)-3-(1'-hydroxyethyl)-4-(1"- hydroxy-methylcarbonyl)ethyl)azetidin-2-one (401 mg, 0.717 mmol) in toluene (15 ml), at 110° C. for 1 hour] was added at ambient temperature triphenylphosphine (207 mg, 0,789 mg). 5-Hydroxy-1-tetralone (116 mg; 0,717 mmol) and DIAD (155 µl; 0.789 mmol) diluted in toluene (1 ml). The resulting solution was stirred at ambient temperature for 15 minutes and partitioned between phosphate buffer (0.5M; pH7, 5 ml) and ethyl acetate (10 ml). The organic phase was evaporated, the residue purified by subjecting to flash chromatography, eluting with ethyl acetate/petroleum ether (60/40) to give allyl (1S,5R,6S,8R)-6-(1-hydroxyethyl)-1-methyl-2-(1-tetralone-5-yloxymethyl)carbapenem-3-carboxylate as an oil (113 mg, 37%).

$^1$H-NMR (CDCl$_3$) δ: 1.28 (d, 3H); 1.36 (d, 3H); 2.13 (t, 2H); 2.62–2.66 (m, 2H); 2.90 (t, 2H); 3.31 (dd, 1H); 3.45–3.5 (m, 1H); 4.11–4.13 (m, 1H); 4.25 (dd, 1H); 4.74–4.84 (m, 2H); 4.81 (d, 1H); 5.28–5.31 (m, 1H); 5.43–5.48 (m, 1H); 5.50 (d, 1H); 5.93–6.03 (m, 1H); 7.02–7.04 (m, 1H); 7.23–7.28 (m, 1H); 7.67–7.69 (m, 1H).

EXAMPLE 2

(1S,5R,6S,8R)-6-(1-Hydroxyethyl)-1-methyl-2-(1-tetralone-7-yloxymethyl)carbapenem-3-carboxylic acid sodium salt The title compound was prepared from allyl (1S,5R,6S, 8R)-6-(1-hydroxyethyl)-1-methyl-2-(1-tetralone-7-yloxymethyl)carbapenem-3-carboxylate using a similar method to that described in Example 1 (yield: 45.7%).

$^1$H-NMR (DMSO-$d_6$+AcOD) δ: 1.05–1.19 (m, 6H); 1.98–2.08 (m, 2H); 2.59 (t, 2H); 2.87 (t, 2H); 3.17–3.29 (m, 2H); 3.91–4.0 (m, 1H); 4.08 (dd, 1H); 4.77 (d, 1H); 5.42 (d, 1H); 7.17 (dd, 1H); 7.28 (d, 1H), 7.36 (d, 1H).

MS (ESI): 430 (MNa+)

The starting material was prepared as follows:

A mixture of 7-methoxy-1-tetralone (5 g; 28 mmol), acetic acid (50 ml) and 48% bromohydric acid (25 ml) was refluxed for 8 hours, poured onto ice and extracted with methylene chloride to give, after evaporation 7-hydroxy-1-tetralone as a solid (4.4 g, 95%).

$^1$H-NMR (DMSO-$d_6$) δ: 1.92–2.04 (m, 2H); 2.48–2.58 (m, 2H), 2.77–2.86 (m, 2H); 6.95 (dd, 1H); 7.16 (d, 1H); 7.22 (d, 1H); 9.56 (s, broad, 1H).

Allyl (1S,5R,6S,8R)-6-(1-hydroxyethyl)-1-methyl-2-(1-tetralone-7-yloxymethyl)carbapenem-3-carboxylate was prepared using a similar method to that described in example 1 but using THF instead of toluene (yield: 38%).

$^1$H-NMR (CDCl$_3$) δ: 1.20–1.38 (m, 6H); 2.06–2.18 (m, 2H); 2.64 (t, 2H); 2.90 (t, 2H); 3.30 (dd, 1H); 3.40–3.50 (m, 1H); 4.17–4.28 (m, 2H); 4.69–4.90 (m, 3H); 5.24–5.52 (m, 3H); 5.92–6.05 (m, 1H), 7.05 (dd, 1H); 7.18 (d, 1H); 7.54 (d, 1H).

MS (ESI): 448 MNa$^+$.

EXAMPLE 3

(1S,5R,6S,8R)-6-(1-Hydroxyethyl)-2-(1-indanone-5-ylthiomethyl)-1-methylcarbapenem-3-carboxylic acid sodium salt The title compound was prepared from the allyl protected compound using a similar method to that described in Example 1 (yield: 28%).

$^1$H-NMR: (DMSO-$d_6$–AcOD) δ: 1.08 (d, 3H); 1.12 (d, 3H); 2.59–2.62 (m, 2H); 3.02–3.06 (m, 2H); 3.16–3.2 (m, 2H); 3.75 (d, 1H); 3.90–3.93 (m, 1H), 3.96 (dd, 1H); 4.95 (d, 1H); 7.33 (d, 1H); 7.50 (s, 1H); 7.51 (d, 1H).

MS: (+ve) FAB 410 (MNa+).

The starting material was prepared as follows:

To a solution of (3S,4R, 1'R,1"R)-1-(allyloxycarbonyl-triphenylphosphoranylidenemethyl)-3-3(1'-hydroxyethyl)-4-(1"-(hydroxymethylcarbonyl)ethyl)azetidin-2-one (450 mg; 0.80 mmol) in methylene chloride (23 ml), under argon atmosphere, was added at −65° C. N-ethyldiisopropylamine (280 ml; 1.61 mmol) and methanesulphonyl chloride (62 δl; 0.80 mmol). After stirring at −65° C. for 30 minutes, 1-indanone-5-thiol (145 mg; 0.88 mmol) and N-ethyldiisopropylamine (140 µl; 0.80 mmol) were added. After 45 minutes, the mixture was extracted with ethyl acetate and purified by flash chromatography using a gradient of $CH_3CN/CH_2Cl_2$ (30–100%) to give (3S,4R, 1'R,1"R)-1-(allyloxycarbonyltriphenylphosphoranylidenemethyl)-3-(1'-hydroxyethyl)-4-(1"-(1-indanone-5-ylthiomethylcarbonyl)ethyl)-azetidine-2-one (447 mg; 78%).

The above compound was cyclised in toluene (20 ml) by heating at 100° C., under argon atmosphere for 45 minutes. After evaporation of the solvent, the residue was purified by subjecting to flash chromatography, eluting with $CH_2Cl_2/CH_3CN$ (80/20 and 60/40) to give allyl (1S,5R,6S,8R)-6-(1-hydroxyethyl)-2-(1-indanone-5-yl-thiomethyl)-1-methylcarbapenem-3-carboxylate (139 mg; 51%). $^1H$ NMR ($CDCL_3$) δ: 1.18 (d, 3H); 1.32 (d, 3H); 2.65–2.7 (m, 2H), 3.05–3.1 (m, 2H); 3.25 (dd, 1H); 3.38–3.41 (m, 1H); 3.51 (d, 1H); 4.12 (dd, 1H); 4.2–4.25 (m, 1H); 4.65–4.81 (m, 2H); 5.0 (d, 1H) 5.25–5.30 (m, 1H); 5.41–5.45 (m, 1H); 5.9–6 (m, 1H); 7.25–7.3 (m, 1H): 7.36 (s, broad, 1H): 7.42–7.7 (m, 1H).

EXAMPLE 4

(1S,5R,6S,8R)-2-(4-Chromanone-7-ylthiomethyl)-6-(1-hydroxyethyl)-1-methylcarbapenem-3-carboxylic acid sodium salt The title compound was prepared from the allyl protected compound using a similar method to that described in Example 1 (yield: 58%).

$^1$H-NMR (DMSO-$d_6$–AcOD) δ: 1.07 (d, 3H); 1.12 (d, 3H); 2.7 (t, 2H), 3.14–3.17 (m, 2H); 3.73 (d, 1H); 4.90–4.93 (m, 1H); 4.97 (dd, 1H); 4.51 (t, 2H); 4.95 (d, 1H); 6.93–6.98 (m, 2H); 7.62 (d, 1H).

MS: (+ve) FAB: 426 (MNa+).

The starting material was prepared as follows:

Allyl (1S,5R,6S,8R)-2-(4-chromanone-7-ylthiomethyl)-6-(1-hydroxyethyl)-1-methylcarbapenem-3-carboxylate was prepared using a similar method to that described in Example 3 for the synthesis of allyl (1S,5R,6R,8R)-6-(1-hydroxyethyl)-2-(1-indanone-5-yl-thiomethyl-1-methylcarbapenem-3-carboxylate.

$^1$H-NMR ($CDCl_3$) δ: 1.18 (d, 3H); 1.32 (d, 3H); 2.77 (t, 2H); 3.25 (dd, 1H); 3.36–3.40 (m, 1H); 3.47 (d, 1H); 4.13 (dd, 1H); 4.2–4.25 (m, 1H); 4.51 (t, 2H); 4.7–4.85 (m, 2H); 4.97 (d, 1H); 5.27–5.30 (m, 1H); 5.42–5.47 (m, 1H) 5.94–5.99 (m, 1H) 6.84–6.90 (m, 2H); 7.75 (d, 1H).

EXAMPLE 5

(1S,5R,6S,8R)-2-(Chromone-6-yloxymethyl)-6-(1-hydroxyethyl)-1-methylcarbapenem-3-carboxylic acid sodium salt The title compound was prepared from the allyl protected compound using a similar method to that described in Example 1 (yield 51.4%).

$^1$-NMR (DMSO-$d_6$+AcOD): 1.10–1.18 (m, 6H); 3.26–3.35 (m, 2H), 3.92–4.01 (m, 1H); 4.12 (dd, 1H); 4.88 (d, 1H); 5.45 (d, 1H); 6.32 (d, 1H); 7.38–7.47 (m, 2H); 7.62 (d, 1H); 8.24 (d, 1H).

MS (ESI): 407 (MH+).

The starting material was prepared as follows:

To a solution of allyl (1S,5R,6S,8R)-6-(1-hydroxyethyl)-2-hydroxymethyl-1-methylcarbapenem-3-carboyxlate [prepared by heating a solution of (3S,4R, 1'R,1"R)-1-allyloxycarbonyltriphenylphosphoranyl-idenemethyl)-3-(1'-hydroxyethyl)-4-(1"-(hydroxymethylcarbonyl)ethyl) azetidin-2-one (500 mg, 0.74 mmol) in toluene (4 ml) at reflux for 1 hour and evaporating the solvent] in toluene (6 ml) was added triphenylphosphine (253 mg, 0.96 mmol), 6-hydroxychromone [J. Med. Chem. 1991, 34, 248] (132 mg, 0.81 mmol) and DEAD (152 µl, 0.96 mmol) dropwise. After 30 minutes at ambient temperature, the mixture was evaporated and purified by flash chromatography, eluting with ethyl acetate/petroleum ether 30/70, to give allyl (1S, 5R,6S,8R)-6-(1-tertbutyldimethylsilyloxyethyl)-2-(chromone-6-yloxymethyl)-1-methylcarbapenem-3-carboxylate as a gum (254 mg, 63.5%).

$^1$H-NMR (CDCL13): δ: 0.08 (s, 6H); 1.22 (d, 3H), 1.25 (d, 3H); 3.27 (dd, 1H); 3.38–3.48 (m, 1H); 4.18–4.27 (m, 2H), 4.70–4.88(m, 3H); 5.23–5.54 (m, 3H); 5.90–6.04 (m, 1H); 6.32 (d, 1H); 7.30 (dd, 1H); 7.42 (d, 1H); 7.64 (d, 1H); 7.84 (d, 1H).

To a solution of the above compound (250 mg, 0.46 mmol) in THF (1 ml) was added, at 4° C., acetic acid (0.265 ml, 4.6 mmol) and tetrabutylammonium fluoride in solution in THF (1.1M; 2.1 ml; 2.3 mmol). The mixture was stirred at 4° C. overnight and at ambient temperature for 4 hours. After the addition of water and neutralising (pH 7) with $NaHCO_3$, the mixture was extracted with ethyl acetate and subjected to flash chromatography, eluting with AcOEt/petroluem ether (70/30), to give allyl (1S,5R,6S,8R)-2-(chromone-6-yloxymethyl)-6-(1-hydroxyethyl)-1-methylcarbapenem-3-carboxylate as a gum (yield 77.3%).

$^1$H-NMR ($CDCl_3$) δ: 1.25 (d, 3H); 1.35 (d, 3H); 3.20 (dd, 1H); 3.40–3.52 (m, 1H); 4.20–4.30 (m, 2H); 4.70–4.91 (m, 3H); 5.23–5.56 (m, 3H); 5.92–6.06 (m, 1H); 6.32 (d, 1H); 7.27 (dd, 1H), 7.42 (d, 1H); 7.63 (d, 1H); 7.84 (d, 1H).

MS (ESI): 448 (MNa$^+$)

EXAMPLE 6

(1S,5R,6S,8R)-6-(1-Hydroxyethyl)-2-(1-indanone-5-yloxy-methyl)-1methylcarbapenem-3-carboxylic acid sodium salt The title compound was prepared from the allyl protected compound using a similar method to that described in Example 1.

$^1$ H-NMR (DMSO-$d_6$+AcOD) δ: 1.1–1.15 (m, 6H); 2.52–2.6 (m, 2H); 3–3.06 (m, 2H); 3.19–3.23 (m, 2H); 3.91–3.98 (m, 1H); 4.07, (dd, 1H); 4.85 (d, 1H); 5.5 (d, 1H); 6.96–7.97 (m, 1H); 7.11 (s, 1H), 7.56 (d, 1H).

The starting material was prepared as follows:

To a solution of 5-methoxy-1-indanone (2 g, 12.3 mmol) in benzene (50 ml) was added $AlCl_3$ (4 g, 31 mmol). The mixture was heated at reflux for 5 hours and extracted with ethyl acetate. The organic phase was evaporated and purified by flash chromatography, eluting with $CH_2Cl_2/CH_3CN$ (90/10) to give 5-hydroxy-1-indanone as a yellow solid (1.65 g; 90%).

¹H-NMR (DMSO-d₆): δ 2.58–2.67 (m, 2H); 2.94–3.01 (m, 2H); 6.79 (dd, 1H), 6.84 (s, 1H); 7.4.7 (d, 1H).

To a solution of allyl (1S,5R,6S,8R)-6-(1-tert-butyl dimethylsilyloxyethyl)-2-hydroxymethyl-1-methylcarbapenem-3-carboxylate [made by heating a solution of (3S,4R,1'R, 1"R)-1-(allyloxycarbonyl(triphenylphoranylidene)methyl)-3-(1-tert-butyldimethylsilyloxyethyl)-4-(1"-(hydroxymethylcarbonylethyl)- azetidin-2-one (552 mg, 82 mmol) in toluene (20 ml), at 110° C. for 1 hour] was added at ambient temperature, tributylphosphine (510 µl, 2 mmol) 5-hydroxy-indanone (133 mg, 0.91 mmol) and ADDP (310 mg; 1.2 mmol). The mixture was stirred at ambient temperature for 3 hours. After addition of hexane, the solid was filtered off and the residue purified by flash chromatography eluting with CH₂Cl₂/CN₃CN (95/5) to give allyl (1S,5R,6S, 8R)-6-(1-(tertbutyldimethylsilyloxy)ethyl)-2-(1-indanone-5-yloxymethyl)-1-methylcarbapenem-3-carboxylate as a foam (347 mg; 80%).

¹H-NMR (CDCl₃): 0.01 (s, 6H); 0.8 (m, 9H); 1.14–1.17 (m, 6H); 2.58–2.61 (m, 2H); 2.99–3.02 (m, 2H); 3.19 (dd, 1H); 3.30–3.38 (m, 1H); 4.12–4.18 (m, 2H); 4.62–4.76 (m, 3H); 5.18–5.21 (m, 1H); 5.35–5.40 (m, 1H); 5.48 (d, 1H); 5.83–5.93 (m, 1H); 6.81–6.85 (m, 2H); 7.61 (d, 1H).

Allyl(1S,5R,6S,8R)-6-(1-hydroxyethyl)-2-(1-indanone-5-yloxymethyl)-1-methylcarbapenem-3-carboxylate was prepared using a similar deprotection method to that described in Example 5 (yield 80%).

¹H-NHR (CDCl₃) δ: 1.24–1.27 (d, 3H); 1.33–1.35 (d, 3H); 2.66–2.69 (m, 2H); 3.07–3.10 (m, 2H); 3.31 (dd, 1H); 3.43–3.48 (m, 1H); 4.23–4.28 (m, 2H); 4.71–4.88 (m, 2H); 4.82 (d, 1H); 5.28–5.31 (m, 1H); 5.44–5.49 (m, 1H); 5.56 (d, 1H); 5.93–6.02 (m, 1H); 6.90–6.92 (m, 2H); 7.69 (d, 1H).

EXAMPLE 7

(1S,5R,6S,8R)-6-(1-Hydroxyethyl)-2-(2-hydroxymethyl-2-methyl-4-chromanone-6-yloxymethyl)-1-methylcarbapenem-3-carboxylic acid sodium salt.

The title compound was prepared from the allyl protected compound using a similar method to that described in Example 1 (yield 51.4).

¹H NMR (DMSO-d₆+CD₃COOD) δ: 1.1–1.17 (m, 6H); 1.25 (s, 3H); 2.58 (dd, 1H); 2.94 (dd, 1H); 3.20–3.31 (m, 2H); 3.46 (d, 1H); 3.54 (d, 1H); 3.90–4.0 (m, 1H); 4.07–4.13 (m, 1H); 4.73 (d, 1H); 5.33 (d, 1H); 6.93 (d, 1H); 7.15–7.21 (m, 2H).

MS (ESI): 454 (MH⁺)

The starting material was prepared as follows:

A solution of 2,4-dihydroxyacetophenone (150 mg; 1 mmol), tert-butyldimethylsilyloxyacetone (206 mg; 1.1 mmol) and pyrrolidine (1.33 µl; 1.6 ml) in toluene (6 ml) was heated at 60° C. for 6 hours in the presence of molecular sieves (4A). After acidification with 1N HCl the mixture was extracted with CH₂Cl₂ and purified by flash chromatography, eluting with ethyl acetate/petroleum ether 20/80, to give 2-(tert-butyldimethylsilyloxymethyl)-6-hydroxy-2-methyl-4-chromanone as an oil (182 mg; 70%).

¹H-NMR (CDCl₃) δ: 0.0 (s, 3H); 0.03 (s, 3H); 0.84 (s, 9H); 1.33 (s, 3H); 2.58 (d, 1H); 2.94 (d, 1H); 3.58 (d, 1H); 3.74 (d, 1H); 6.81 (d, 1H); 7.01 (dd, 1H); 7.25 (d, 1H).

Allyl (1S,5R,6S,8R)-2-(2-(tert-butyldimethylsilyloxymethyl)-2-methyl-4-chromanone-6-yloxymethyl)-6-(1-hydroxyethyl)-1-methylcarbapenem-3-carboxylate was prepared using a similar method to that described in Example 5 but using the compound from the previous step in place of 6-naphthol.

¹H-NMR (CDCl₃) δ: –0.03 (s, 3H); 0.00 (s, 3H); 0.8 (s, 9H); 1.2–1.35 (m, 9H); 2.56 (d, 1H); 2.92 (d, 1H); 3.26 (dd, 1H); 3.4–3.48 (m, 1H); 3.56 (d, 1H); 3.72 (d, 1H); 4.18–4.28 (m, 2H); 4.62–4.83 (m, 3H); 5.23–5.45 (m, 3H); 5.9–6.0 (m, 1H); 6.81 (d, 1H); 7.02 (dd, 1H); 7.27 (d, 1H).

Allyl (1S,5R,6S,8R)-2-(2-hydroxymethyl-2-methyl-4-chromanone-6-yloxymethyl)-6-(1-hydroxyethyl)-1-methylcarbapenem-3-carboxylate was prepared using a similar deprotection method to that described in Example 5 (yield 90%).

¹H-NMR (CDCl₃) δ: 1.23 (d, 3H); 1.33 (s+d, 6H); 2.51 (d, 1H); 3.12 (d, 1H); 3.3 (dd, 1H); 3.4–3.5 (m, 1H); 3.58–3.8 (m, 2H); 4.2–4.3 (m, 2H); 4.7–4.9 (m, 3H); 5.27–5.50 (m, 3H); 5.9–6.02 (m, 1H); 6.88 (d, 1H); 7.10 (dd, 1H); 7.35 (d, 1H).

MS (ESI): 494 (MNa+).

EXAMPLE 8

(1S,5R,6S,8R)-6-(1-Hydroxyethyl)-1-methyl-2-(1-tetralone-7-ylthiomethyl)carbapenem-3-carboxylic acid sodium salt The title compound was prepared from the allyl protected compound using a similar method to that of Example 1 (yield 16.7%).

¹H-NMR (DMSO-d₆–AcOD): δ: 1.08 (d, 3H); 1.13 (d, 3H); 1.97–2.08 (m, 2H); 2.60 (t, 2H); 2.92 (t, 2H); 3.20 (dd, 1H); 3.23–3.33 (m, 1H); 3.63 (d, 1H); 3.88–3.95 (m, 1H); 4.00 (dd, 1H); 4.72 (d, 1H); 7.30 (d, 1H); 7.53 (dd, 1H); 7.80 (d, 1H).

MS (ESI): 446 (MNa+).

A mixture of 7-hydroxy-1-tetralone (4 g, 24.6 mmol), K₂CO₃ (3.4 g, 24.6 mmol) in DMF (45 ml) was heated at 80° C. for 1 hour. At ambient temperature, N,N-dimethylthiocarbonamoyl chloride (3.65 g; 29.5 mmol) were added. After stirring for 1.5 hours, the solution was poured onto ice and extracted with ethyl acetate to give, after flash chromatography (CH₂Cl₂/CH₃CN (95/5)), dimethylthiocarbamic acid 0-(1-tetralone-7-yl) ester.

¹H-NMR (DMSO-d₆) δ: 2.03–2.13 (m, 2H); 2.62 (t, 2H); 2.96 (t, 2H); 3.32–3.40 (m, 6H); 7.26 (dd, 1H); 7.39 (d, 1H); 7.47 (d, 1H).

The above compound (3.8 g; 15.6 mmol) was heated at 240° C. for 30 minutes. The residue was purified by flash chromatography eluting with AcOEt/petroleum ether (40/60), to give dimethylthiocarbamic acid S-(1-tetralone-7-yl) ester as an oil (540 mg; 14%).

¹H-NMR (CDCl₃) δ: 2.02–2.1 (m, 2H); 2.65 (t, 2H); 2.94 (t, 2H); 2.95–3.10 (m, 6H); 7.28 (d, 1H); 7.59 (dd, 1H); 8.13 (d, 1H).

A mixture of dimethylthiocarbamic acid S-(tetralone-7-yl) ester (400 mg; 1.6 mmol) and NaOH (128 mg; 3.2 mmol) in methanol (2 ml) was heated at reflux for 30 minutes. After evaporation to dryness, the residue was acidified to pH2 and extracted with CH₂Cl₂ to give, after removal of the solvent 1-tetralone-7-thiol as a gum which was used in the next step without further purification (280 mg; 100%).

¹H-NMR (CDCl₃) δ: 2.09–2.19 (m, 2H); 2.64 (t, 2H); 2.85–2.95 (m, 2H); 7.21 (d, 1H); 7.62 (dd, 1H); 8.10 (d, 1H).

Allyl (1S,5R,6S,8R)-6-(1-hydroxyethyl)-1-methyl-2-(1-tetralone-7-yl)thiomethyl)carbapenem-3-carboxylate was prepared using a similar method to that of Example 7 (yield 30%).

¹H-NMR (CDCl₃) δ: 1.25 (d, 3H); 1.30 (d, 3H); 2.10–2.17 (m, 2H); 2.60–2.66 (m, 2H); 2.90–2.99 (m, 2H); 3.22 (dd, 1H); 3.25–3.40 (m, 2H); 4.10 (dd, 1H); 4.15–4.20 (m, 1H); 4.65–4.9 (m, 3H); 5.25–5.45 (m, 2H); 5.87–6.02 (m, 1H); 7.25–7.3 (m, 1H); 7.4–7.44 (m, 1H); 7.82 (d, 1H).

EXAMPLE 9

(1S,5R,6S,8R)-6-(1-Hydroxyethyl)-1-methyl-2-(1-tetralone-6-ylthiomethyl)carbapenem-3-carboxylic acid sodium salt The title compound was prepared from the allyl protected compound using a similar method to that of Example 1.

¹H-NMR (DMSO-d₆+AcOD) δ: 1.05–1.15 (m, 6H); 1.97–2.06 (m, 2H); 2.52–2.60 (m, 2H); 2.85–2.93 (m, 2H); 3.18–3.25 (m, 2H); 3.77 (d, 1H); 3.88–3.97 (m, 1H); 4.02 (dd, 1H); 4.80 (d, 1H); 7.21–7.25 (m, 2H); 7.77 (d, 1H).

MS (ESI): 424 (MH+).

The starting material was prepared as follows:

Tri-n-butylphosphine (960 µl, 3.78 mmol), 1-tetralone-6-thiol (Chem. Pharma. Bull. 1984, 32, 130) (331 mg, 1.82 mmol) and ADDP (540 mg, 2.1 mmol) were added to a solution of allyl (1S,5R,6S,8R)- 6-(1-hydroxyethyl)-2-hydroxymethyl-1-methylcarbapenem-3-carboxylate (prepared from 800 mg, 1.4 mmol of (3S,4R, 1'R, 1"R)-1-(allyloxycarbonyl(triphenylphosphoranylidene)methyl)-3-(1'-hydroxyethyl)-4-(1"-(hydroxymethylcarbonyl)ethyl)azetidin-2-one using the method described in Example 1) in toluene (50 ml).

The mixture was left overnight at ambient temperature, hexane was added, the precipitate filtered off and the filtrate evaporated under vacuum. The product was purified by chromatography, eluting with ethyl acetate/petroleum ether 70/30, to give allyl (1S,5R,6S,8R)-6-(1-hydroxyethyl)-1-methyl-2-(1-tetralone-6-ylthiomethyl)carbapenem-3-carboxylate as a gum (77 mg, 12.4%).

¹H-NMR (CDCl₃) δ: 1.18 (d, 3H); 1.34 (d, 3H); 2.07–2.15 (m, 2H); 2.60–2.68 (m, 2H); 2.85–2.93 (m, 2H); 3.25 (dd, 1H); 3.32–3.45 (m, 1H); 3.47 (d, 1H); 4.10–4.25 (m, 2H); 4.65–4.83 (m, 2H); 5.0 (d, 1H); 5.25–5.43 (m, 2H); 5.87–5.98 (m, 1H); 7.10–7.25 (m, 2H); 7.90 (d, 1H).

EXAMPLE 10

(1S,5R,6S,8R)-6-(1-hydroxyethyl)-1-methyl-2-(1-tetralone-6-yloxymethyl)carbapenem-3-carboxylic acid sodium salt The title compound was prepared from the allyl protected compound using a similar deprotection method to that of Example 1.

¹H-NMR (DMSO-d₆+AcOD) δ: 1.10–1.17 (m, 6H); 1.95–2.05 (m, 2H), 2.87–2.93 (m, 3H); 3.23–3.30 (m, 3H); 3.90–4.02 (m, 1H); 4.13 (dd, 1H); 5.85 (d, 1H); 5.37 (d, 1H); 6.87–6.90 (m, 2H); 7.82 (d, 1H).

MS (+ve) FAB 386 (MH+).

The starting material was prepared as follows:

A mixture of 6-methoxy-1-tetralone (5 g, 28.4 mmol) in acetic acid (50 ml) and 48% bromhydric acid (25 ml) was heated at reflux for 7 hours. After extraction with CH₂Cl₂ and evaporation, the residue was purified by flash chromatography (AcoEt/petroleum ether 45/55) to give 6-hydroxy-1-tetralone as a foam (3.9 g; 84.7%).

¹H-NMR (DMSO-d₆) δ: 1.95–2 (m, 2H); 2.46–2.52 (m, 2H); 2.83 (t, 2H); 6.64 (d, 1H); 6.70 (dd, 1H); 7.73 (d, 1H).

Allyl(1S,5R,6S,8R)-6-(1-hydroxyethyl)-1-methyl-2-(1-tetralone-6-yloxymethyl)carbapenem-3-carboxylate was prepared using a similar method to that of Example 1 (yield 15.8%).

¹H-NMR (CDCl₃) δ: 1.24 (d, 3H); 1.34 (d, 3H); 2.08–2.15 (m, 2H); 2.55–2.63 (m, 2H); 2.85–2.94 (m, 2H); 3.30 (dd, 1H); 3.40–3.50 (m, 1H); 4.20–4.28 (m, 2H); 4.65–4.90 (m, 3H); 5.25–5.53 (m, 3H); 5.90–6.05 (m, 1H); 6.72 (d, 1H); 6.83 (dd, 1H); 8.00 (d, 1H).

EXAMPLE 11

(1S,5R,6S,8R)-2-(4-Chromanone-7-yloxymethyl)-6-(1-hydroxyethyl)-1-methylcarbapenem-3-carboxylic acid sodium salt The title compound was prepared from the allyl protected compound using a similar method to that of Example 1 (yield 52%).

¹H-NMR (DMSO-d₆+AcOD) δ: 1.10 (d, 3H): 1.13 (d, 3H), 2.70 (t, 2H); 3.10–3.23 (m, 2H); 3.90–3.98 (m, 1H); 4.06 (dd, 1H); 4.50 (t, 2H); 4.85 (d, 1H); 5.48 (d, 1H); 6.56 (d, 1H); 6.67 (dd, 1H); 7.70 (d, 1H).

Allyl (1S,5R,6S,8R)-6-(1-tert-butylmethylsilyloxyethyl)-2(4-chromanone-7-yl-oxymethyl)-1-methylcarbapenem-3-carboxylate was prepared using a similar method to that of Example 5 (yield 80%).

¹H-NMR (CDCl₃) δ: 0.06 (s, 6H); 0.86 (s, 9H); 1.20–1.27 (m, 6H); 2.72 (t, 2H); 3.24 (dd, 1H); 3.31–3.40 (m, 1H); 4.16–4.26 (m, 2H); 4.5 (t, 2H); 4.66–4.80 (m, 3H); 5.21–5.48 (m, 3H); 5.86–5.98 (m, 1H); 6.41 (d, 1H); 6.57 (dd, 1H); 7.82 (d, 1H).

Allyl (1S,5R,6S,8R)- 2-(4-chromanone- 7-yloxymethyl)-6(1-hydroxyethyl)-1-methylcarbapenem- 3-carboxylate was preapred using a similar method for the removal of the silyl protecting group as that of Example 5 (yield 60%).

¹H-NMR (CDCl₃) δ: 1.23 (d, 3H); 1.32 (d, 3H); 2.76 (t, 2H); 3.30 (dd, 1H); 3.38–3.48 (m, 1H); 4.20 –4.30 (m, 2H); 4.51 (t, 2H); 4.70–4.90 (m, 3H); 5.30–5.55 (m, 3H); 5.90–6.04 (m, 1H); 6.43 (d, 1H); 6.59 (dd, 1H); 7.84 (d, 1H).

MS (+ve), FAB: 428 (MH+).

EXAMPLE 12

(1S,5R,6S,8R)-6-(1-Hydroxyethyl)-1-methyl-2-(1-methylindolin-2-one-5-ylthiomethyl)carbapenem-3-carboxylic acid sodium salt The title compound was prepared from the allyl protected compound using a similar method to that of Example 1 (yield 25%).

¹H-NMR (DMSO-d₆+AcOD) δ: 1.05 (d, 3H); 1.12 (d, 3H); 3.10 (s, 3H); 3.16 (dd, 1H); 3.20–3.30 (m, 1H); 3.47–3.52 (m, 2H), 3.46 (d, 1H); 3.88–3.95 (m, 1H); 4.03 (dd, 1H); 4.61 (d, 1H); 6.90 (d, 1H); 7.28–7.32 (m, 2H).

Allyl (1S,5R,6S,8R)-6-(1-hydroxyethyl)-1-methyl-2-(1-methylindolin-2-one-5-ylthiomethyl)carbapenem-3-carboxylate was prepared using a similar method to that of Example 9 (yield 90%).

¹H-NMR (CDCl₃) δ: 1.15 (d, 3H); 1.33 (d, 3H); 3.20–3.28 (m, 4H); 3.30 (d, 1H); 3.40–3.50 (m, 3H); 4.15–4.27 (m, 2H); 4.45–4.62 (m, 2H); 4.71 (d, 1H); 5.20–5.35 (m, 2H); 5.80–5.90 (m, 1H); 6.71 (d, 1H); 7.24–7.35 (m, 2H).

EXAMPLE 13

(1S,5R,6S,8R)-6-(1-Hydroxyethyl)-1-methyl-2-(2-oxo1,2,3,4-tetrahydroquinolin-6-ylthiomethyl)carbapenem-3-carboxylic acid sodium salt The title compound was prepared from the allyl protected compound using a similar method to that of example 1 (yield 36%).

1H NMR (DMSO-d$_6$+AcOD) δ: 1.04 (d, 3H); 1.12 (d, 3H); 2.43 (t, 2H; 2.83 (t, 2H); 3.16 (dd, 1H); 3.20–3.30 (m, 1H); 3.45 (d, 1H); 3.90–3.97 (m, 1H); 4.0 (dd, 1H); 4.64 (d, 1H); 6.77 (d, 1H); 7.13–7.18 (m, 2H); 10.11 (s, 1H).

MS (ESI): 447 (M+Na$^+$).

Allyl (1S,5R,6S,8R)-6-(1-hydroxyethyl)-1-methyl-2-(1,2,3,4-tetrahydroquinolin-2-one-6-ylthiomethyl)carbapenem-3-carboxylate was prepared from the allyl protected compound using a similar method to that of Example 9 (yield 98%).

$^1$H-NMR (CDCl$_3$) δ: 1.15 (d, 3H); 1.33 (d, 3H); 2.58–2.64 (m, 2H); 2.85–2.95 (m, 2H); 3.24 (dd, 1H); 3.3 (d, 1H); 3.35–3.45 (m, 1H); 4.17 (dd, 1H); 4.20–4.28 (m, 1H); 4.52–4.68 (m, 2H); 4.73 (d, 1H); 5.22–5.40 (m, 2H); 5.80–5.93 (m, 1H); 6.62 (d, 1H); 7.15–7.28 (m, 2H).

EXAMPLE 14

(1S,5R,6S,8R)-6-(1-Hydroxyethyl)-1-methyl-2-(1-methyl-2-oxo1,2,3,4-tetrahydroquinolin-6-ylthiomethyl)carbapenem-3carboxylic acid sodium salt The title compound was prepared from the allyl protected compound using a similar method to that of Example 1 (yield 33%).

$^1$H-NMR (DMSO-d$_6$+AcOD): δ: 1.05 (d, 3H); 1.12 (d, 3H); 2.48–2.53 (m, 2H); 2.77–2.84 (m, 2H); 3.16 (dd, 1H); 3.22 (s, 3H); 3.20–3.30 (m, 1H); 3.5 (d, 1H); 3.9–3.97 (m, 1H); 4.00 (dd, 1H); 4.72 (d, 1H); 7.00 (d, 1H); 7.20–7.28 (m, 2H).

MS (+ve)FAB: 439 (MH+).

Allyl (1S,5R,6S,8R)-6-(1-hydroxyethyl)-1-methyl-2-(1-methyl-1,1,2,3,4-tetrahydroquinolin-2-one-6-ylthiomethyl)-carbapenem-3-carboxylate was prepared using a similar method to that of Example 9 (yield 96%).

$^1$H-NMR (CDCl$_3$) δ: 1.16 (d, 3H); 1.33 (d, 3H); 2.60–2.66 (m, 2H); 2.8–2.93 (m, 2H); 3.23 (dd, 1H); 3.30–3.31 (m, 1H); 3.32 (s, 3H); 4.17 (dd, 1H); 4.20–4.25 (m, 1H); 4.5–4.65 (m, 2H); 4.76 (d, 1H); 5.20–5.37 (m, 2H); 5.8–5.93 (m, 1H); 6.86 (d, 1H); 7.18 (d, 1H); 7.24–7.28 (m, 1H).

MS (+ve) FAB: 457 (MH$^+$).

EXAMPLE 15

(1S,5R,6S,8R)-6-(1-Hydroxyethyl)-1-methyl-2-(4-thiochromanone-7-ylthiomethyl)carboxylate acid sodium salt was prepared from the allyl protected compound using a similar method to that of Example 1 (yield 49%)

$^1$H-NMR (DMSO-d$_6$–AcOD) δ: 1.08 (d, 3H); 1.12 (d, 3H); 2.84–2.87 (m, 2H); 3.16–3.19 (m, 2H); 3.28–3.31 (m, 2H); 3.75 (d, 1H); 3.9–3.94 (m, 1H); (m, 1H); 3.97 (dd, 1H); 4.92 (d, 1H); 7.13 (dd, 1H); 7.25 (d, 1H); 7.83 (d, 1H).

MS (+re) FAB: 442 (MNa$^+$).

Allyl (1S,5R,6S,8R)-6-(1-hydroxyethyl)-1-methyl-2-4-thiochromanone-7-ylthiomethyl)carbapenem-3-carboxylate was prepared using a similar method to that of Example 3.

$^1$H-NMR (CDCl$_3$) δ: 1.17 (d, 3H); 1.32 (d, 3H); 2.92–2.96 (m, 2H); 3.20–3.26 (m, 3H); 3.36–3.40 (m, 1H); 3.45 (d, 1H); 4.09–4.14 (m, 1H); 4.20–4.24 (m, 1H); 4.69–4.87 (m, 2H); 5.0 (d, 1H); 5.28–5.30 (m, 1H); 5.43–5.48 (m, 1H); 5.93–6.01 (m, 1H); 7.03; (dd, 1H); 7.15 (d, 1H); 7.96 (d, 1H);

EXAMPLE 16

(1S,5R,6S,8R)-2-((2-Benzoylmethyl)-1-indanone-4-yloxymethyl)-6-(1-hydroxyethyl)-1-methylcarbapenem-3-carboxylic acid sodium salt The title compound was prepared from allyl (1S,5R,6S,8R)2-(2-benzoylmethyl)-1-indanone-4-yloxymethyl)-6-(1-hydroxyethyl)-1-methylcarbapenem-3-carboxylate using a similar method to that described in Example 1 (yield: 48%).

$^1$H-NMR: (DMSO-d$_6$–AcOD) δ: 1.1 (m, 6H);2.7(dd, 1H);3.05(m, 1H);3.25(m, 2H);3.3(m, 1H);3.5–3.7(m, 2H);3.95(m, 1H);4.1(m, 1H);4.9(d, 1H);5.5(d, 1H);7.25(m, 2H);7.4(t, 1H);7.55(t, 2H);7.S5(t, 1H);8.0(d, 2H).

The starting material was prepared as follows:

To a solution of 4-hydroxy-1-indanone (1 g; 6.7 mmol) in THF were added, at ambient temperature and under argon, powdered 1,3,5-trioxane (1.2 g; 13.4 mmol) and N-methyl-N-phenylammonium trifluoroacetate (2.9 g; 13.4 mmol). The suspension was refluxed for 4 hours. Ether was added to the mixture and the resulting precipitate was filtered off. The organic phase was washed with water, dried over MgSO$_4$, filtered and evaporated. The residue obtained was purified by flash chromatography on silica gel, eluting with petroleum ether/ethyl acetate (8/2) to give 4-hydroxy-2-methylene-1-indanone as a beige solid (0.76 g; 70%).

$^1$H-NMR: (DMSO-d$_6$) δ: 2.5(s, 2H);3.6(s, 1H);5.75(s, 1H);6.15(s, 1H);7.1(d, 1H);7.2(d, 1H);7.3(t, 1H).

To a solution of the above compound (0.2 g; 1.24 mmol) in ethanol were added, at ambient temperature and under argon: benzaldehyde (0.15ml; 1.49 mmol), triethylamine (52 µl 1; 0.37 mmol), and 3,4-dimethyl-5,-(2-hydroxyethyl)thiazolium iodide (35 mg; 0.12 mmol) as a catalyst. The mixture was heated at reflux for 15 hours. The solution was evaporated and CH$_2$Cl$_2$ added to the residue, washed with 1N HCl, then a saturated solution of NaHCO$_3$ and finally a saturated solution of NaCl. The organic phase was dried over MgSO$_4$, filtered and evaporated. The residue was purified by flash chromatography on silica gel, eluting with petroleum ether/ethyl acetate (9/1) to give 2-benzoylmethyl-4-hydroxy-1-indanone as a white solid (0.26 g; 78%).

$^1$H-NMR: (DMSO-d$_6$) δ: 2,65(dd, 1H);3.05(m, 1H);3.25(dd, 1H);3.45(dd, 1H); 3.65(dd, 1H);7.05(d, 1H);7.1(d, 1H);7.25(t, 1H);7.55(t, 2H);7.65(t, 1H);7.95 (d, 2H);9.9 (s, 1H).

Allyl (1S,5R,6S,8R)-2-((2-benzoylmethyl)-1-indanone-4-yloxymethyl)-6-(1-hydroxyethyl)-1-methylcarbapenem-3-carboxylate was prepared using a similar method to that described in Example 5 but using 2-benzoylmethyl-4-hydroxy-1-indanone instead of 6-hydroxychromone, to produce (1S,5R,6S,8R)-2-(2-(benzoylmethyl)-1-indanone-4-yloxymethyl)-6-(1-hydroxyethyl)-1-methylcarbapenem-3carboxylate (yield: 57%).

$^1$H-NMR:(CDCl$_3$) δ: 25(d, 3H);1.35(d, 3H);2.7(dd, 1H);B.2–3.3(m, 3H);3.5(m, 2H);4.25(m, 2H);4.7–4.9(m,

3H);5.3(dd, 1H);5.45(dd, 1H);5.55(dd, 1H);5.95(m, 1H);7.05–7.6(m, 6H);8.0(d, 2H).

EXAMPLE 17

(1S,5R,6S,8R)-6-(1-Hydroxyethyl)-2-(1-indanone6-ylthiomethyl)-1-methylcarbapenem-3-carboxylic acid sodium salt The title compound was prepared from allyl (1S,5R,6S, 8R)-6-(1-hydroxyethyl)-2-(1-indanone-6-ylthiomethyl)-1-methylcarbapenem-3-carboxylate using a similar method to that described in Example 1 (yield: 42%).

$^1$H-NMR:(DMSO-$d_6$+AcOD)S: δ: 1.05(d, 3H);1.15(d, 3H);2.65(t, 2H);3.05(t, 2H);3.15(dd, 1H);B.25(m, 1H);3.65(d, 1H);B.9(m, 1H);3.95(dd, 1H);4.75(d, 1H);7.45–7.65(m, 3H).

The starting material was prepared as follows:

To a solution of 6-hydroxy-1-indanone (2 g; 13.5 mmol) and pyridine (1.6 ml; 20.2 mmol) in $CH_2Cl_2$, was added, dropwise at 60° C. and under argon, triflic anhydride (2.7 ml; 16.1 mmol). After 15 minutes the solution was stirred at 0° C. for one hour. More $CH_2Cl_2$ was added and the solution washed with a saturated aqueous solution of $NaHCO_3$ and then a saturated aqueous solution of NaCl. The organic phase was dried over $MgSO_4$, filtered and evaporated. The residue was purified by flash chromatography on silica gel, eluting with petroleum ether/ethyl acetate (8/2) to give 6-trifluormethanesulphonyl1-indanone as a white solid (3.3 g; 89%).

$^1$H-NMR: (CDCl$_3$) δ:2.8(t, 2H);7.5(dd, 1H); 7.6(d, 1H); 7.65(d, 1H);7.65(d, 1H).

To a solution of the above compound (1.5 g; 5.35 mmol) and tetrakis (triphenylphosphine) palladium (0.35 g; 0.32 mmol) in benzene was added a solution of sodium triisopropylsulfidosilane (1.2 g; 5.8 mmol) in THF. The solution, which turned dark brown, was heated for 4 hours at 90° C. The resulting residue was taken up by ether, and washed in water and a saturated aqueous solution of NaCl. The organic phase was dried over $MgSO_4$, filtered and evaporated. The residue was purified by flash chromatography on silica gel, eluting with petroleum ether/ethyl acetate (9/2) to give 6-(tri(isopropyl)silylthio)-1-indanone (1.1 g; 64%).

$^1$H-NMR: (CDCl$_3$) δ:1.1(d, 18H);1.25(m, 1H);2.7(t, 2H);3.1(t, 2H);7.3–7.85(m, 3H).

To a solution of the above compound (0.5 g; 1.56 mmol) in a minimum of THF, was added, at 0° C. and under argon, tetrabutylammonium fluoride in a solution of THF (1.1M; 1.4 ml; 1.56 mmol). The solution was mixed in ethyl acetate and washed with water. The aqueous phase was acidified at 0° C. with 2N HCl to pH 4.5. The resulting precipitate was washed with water and filtered to give 1-indanone-6-thiol as a white solid (95 mg; 40%).

$^1$H-NMR: (CDCl$_3$) δ: 2.7(t, 2H);3.1(t, 2H);3.55(s, 1H);7.35(d, 1H);7.45(dd, 1H);7.65(d, 1H).

Allyl (1S,5R,6S,8R)-2-(1-indanone-6-ylthiomethyl)-1-methyl6-(1-(tertbutyldimethylsilyloxy)ethyl)carbapenem-3-carboxylate was prepared using a similar method to that described in Example 3 using (3S,4R, 1'R,1"R)-1-(allyloxycarbonyl(triphenylphosphoranylidene)-methyl-4-(1"-(hydroxymethylcarbonyl)ethyl)-3-(1'-(tertbutyl-dimethylsilyloxy)ethyl)azetidin- 2-one in place of (3S,4R, 1'R,1"R)-1-(allyloxycarbonyl(triphenylphosphoranylidine)methyl)-3-(1'-hydroxyethyl)-4-(1"-hydroxymethylcarbonylethyl)azetidin2-one and using 1-indanone-6-thiol plus tributyl phosphine/water and DMF instead of 1-indanone-5-thiol (yield: 75%).

$^1$H-NMR:(CDCl$_3$) δ: 0(s, 6H);0.85(s, 9H);1.1(d, 3H);1.25(d, 3H);2.7(t, 2H);3.1(t, 2H);3.2(dd, 1H);3.35(m, 1H);3.4(d, 1H);4.05(dd, 1H);4.15(m, 1H);4.55–4.75(m, 2H);4.85(d, 1H);5.25(d, 1H);5.4(d, 1H);5.9(m, 1H);7.35(d, 1H);7.55(dd, 1H);7.75(s, 1H).

To a solution of the above compound (312 mg; 0.57 mmol) in a minimum of THF was added at 0° C., acetic acid (0.19 ml; 3.46 mmol) and tetrabutylammonium fluoride in solution in THF (1.1M; 1.6 ml; 1.73 mmol). The mixture was stirred at 4° C. for 2 days. After addition of phosphate buffer, the mixture was extracted with ethyl acetate and subjected to flash chromatography, eluting with ethyl acetate/ petroleum ether (50/50), to give allyl (1S,5R,6S, 8R)-6-(1-hydroxyethyl)-2-(1-indanone-6-ylthiomethyl)-1-methylcarbapenem-3-carboxylate (yield: 63%).

$^1$H-NMR:(CDCl$_3$) δ:15(d, 3H);1.3(d, 3H);2.7(t, 2H);3.1(m, 2H);3.25(dd, 1H);3.35(d+m, 2H); 4.1–4.25(m, 2H);4.65(m, 2H)4.9(d, 1H);5.25(dd, 1H);5.4(dd, 1H);5.9(m, 1H);7.35(d, 1H);7.55(dd, 1H);7.8(d, 1H).

EXAMPLE 18

(1S,5R,6S,8R)-6-(1-Hydroxyethyl)-1-methyl-2-(2-(2-thienylmethylene)-1-indanone-4-yloxymethyl) carbapenem-3-carboxylic acid sodium salt The title compound was prepared from allyl (1S,5R,6S, 8R)-6-(1-hydroxyethyl)-1-methyl-2-(2-(2-thienylmethylene)- 1-indanone-4-yloxymethyl)carbapenem-3-carboxylate using a similar method to that described in Example 1 (yield: 52%).

$^1$H-NMR:(DMSO-$d_6$+AcOD) δ: 0(d, 3H);1.05(d, 3H);3.1(dd, 1H);3.15(m, 1H);3.7(s, 2H);3.85(m, 1H);3.95(dd, 1H);4.85(d, 1H);5.5(d, 1H);;7.15–7.4(m, 4H);7.6(d, 1H);7.7(s, 1H);7.85(d, 1H).

The starting material was prepared as follows:

To 4-methoxy-1-indanone (0.1 g; 0.62 mmol) were added thiophene-2-carboxaldehyde (87.5 μl ; 0.93 mmol), piperidine (18.5 μl ; 0.18 mmol) and acetic acid (10.7 μl ; 0.18 mmol). After heating at 130° C. for 90 minutes the mixture was taken up in $CH_2Cl_2$, washed with water and purified by flash chromatography, eluting with petroleum ether/ethyl acetate (95/5) to give 4-methoxy-2-(2-thienylmethylene)-1-indanone (140 mg; 90%).

$^1$H-NMR: (CDCl$_3$) δ: 3.85(s, 2H);3.95(s, 3H);7.05(d, 1H);7.15(t, 1H);7.4(t, 1H);7.45(d, 1H);7.6(d, 1H);7.7(d, 1H);7.85(s, 1H).

To a solution of the above compound (410 mg; 1.61 mmol) in $CH_2Cl_2$ (10 ml) was added, at −65° C., boron tribromide (0.7 ml; 8 mmol). After 30 minutes the solution was stirred at 0° C. for one hour, then extracted and purified using flash chromatography, eluting with petroleum ether/ ethyl acetate (60/40) to give 4-hydroxy-2-(2-thienyl methylene)-1-indanone (260 mg; 67%).

$^1$H-NMR: (DMSO-$d_6$) δ: 3.8(s, 2H);7.0–7.4(m, 4H);7.7–8.0(m, 3H).

Allyl (1S,5R,6S,8R)-1-methyl-6-(1-(tertbutyldimethylsilyloxy)ethyl)-2-(2-(2-thienylmethylene)-1-indanone-4-yloxymethyl)carbapenem-3-carboxylate was prepared using a similar method to that described in Example 5 but using 4-hydroxy-2-(2-thienylmethylene)-1-indanone instead of 6-hydroxychromone (yield: 62%).

¹H-NMR:(CDCl₃) δ:35(d, 3H);1.4(d, 3H);1.7(d, 1H); 3.35(dd, 1H);3.5(m, 1H);3.85(s, 2H);4.25(m, 2H);4.65–4.9(m, 2H);4.95(d, 1H);5.3(d, 1H);5.45(d, 1H);5.6(d, 1H);5.95(m, 1H);7.05(d, 1H);7.15(t, 1H);7.35(t, 1H);7.45(d, 1H);7.55(d, 1H);7.6(d, 1H);7.9(s, 1H).

Using the above compound allyl (1S,5R,6S,8R)-6-(1-hydroxyethyl)-1-methyl-2-(2-(2-thienylmethylene)-1 -indanone-4-yloxymethyl)carbapenem-3-carboxylate was prepared using a similar method to that described in Example 5 (yield: 69%).

¹H-NMR:(CDCl₃) δ: 0(s, 6H);0.8(s, 9H);1.15(d, 3H);1.25(d, 3H);3.2(dd, 1H);3.35(m, 1H);4.15(m, 2H);4.6–4.8(m, 2H);4.8(d, 1H);5.15(dd, 1H);5.35(dd, 1H);5.45(d, 1H);5.85(m, 1H);7.0(d, 1H);7.1(t, 1H);7.3(d, 1H);7.35(d, 1H);7.4(d, 1H);7.45(d, 1H);7.8(s, 1H).

EXAMPLE 19

(1S,5R,6S,8R)-6-(1-Hydroxyethyl)-1-methyl- 2-(2-(2-thienylmethylene)-1-tetralone-5-yloxymethyl) carbapenem-3-carboxylic acid sodium salt The title compound was prepared from allyl (1S,5R,6S,8R)6-(1-hydroxyethyl)-1-methyl-2-(2-(2-thienylmethylene)-1-tetralone- 5-yloxymethyl)carbapenem-3-carboxylate using a similar method to that described in Example 1 (yield: 36.5%).

¹H-NMR:(DMSO-d₆+AcOD) δ: 1.15(m, 6H);3.0(t, 2H);3.15(t, 2H);3.25(m, 1H);B.35(m, 1H); 3.95(m, 1H);4.15(dd, 1H);4.S5(d, 1H);5.45(d, 1H);7.25(t, 2H);7.35(t, 1H);7.55–7.65(m, 2H);7.9(d, 1H);7.92(s, 1H).

The starting material was prepared as follows:

A mixture of 5-methoxy-1-tetralone (1 g; 5.67 mmol), thiophene-2-carboxaldehyde (800 μl 8.51 mmol), piperidine (168 μl; 1.7 mmol) and acetic acid (97 μl; 1.7 mmol) was heated at 130° C. for 2 hours. The mixture was taken up in CH₂C₂ and washed in water and in a saturated aqueous solution of NaCl. The organic phase was dried over MgSO₄, filtered and evaporated. The residue was purified by flash chromatography on silica gel, eluting with petroleum ether/ethyl acetate (95/5) to give 5-methoxy-2-(2-thienylmethylene)-1-tetralone (1.2 g; 80%)

¹H-NMR:(CDCl₃) δ: 3.0(t, 2H);3.2(t, 2H);3.9(s, 3H);7.8(m, 7H).

To a solution of the above compound (1 g; 3.7 mmol) in CH₂Cl₂ was added, dropwise at –65° C. and under argon, boron tribromide (1.7 ml; 18.5 mmol). After 30 minutes, at 0° C., the reaction had finished. Water was added at 0° C. and the aqueous phase was neutralised using a saturated aqueous solution of NaHCO₃. The product was extracted using CH₂Cl₂. The organic phase was washed in a saturated solution of NaCl, dried over MgSO₄, filtered and evaporated. The residue was purified by flash chromatography on silica gel, eluting with petroleum ether/ethyl acetate (85/15) to give 5-hydroxy-2-(2-thienylmethylene)1-tetralone (0.4 g; 42%).

¹H-NMR; (DMSO-d₆) δ: 2.9(t, 2H);3.1(t, 2H);7.05(d, 1H);7.15–7.25(m, 2H);7.45(d, 1H);7.6(d, 1H);7.85(d, 2H);9.85(s, 1H).

Allyl (1S,5R,6S,8R)-6-(1-hydroxyethyl)-1-methyl- 2-(2-(2-thienylmethylene)-1-tetralone- 5-yloxymethyl)-carbapenem-3-carboxylate was prepared using a similar method to that described in Example 1 but using 5-hydroxy-2-(2-thienylmethylene)1-tetralone instead of 5-hydroxy-1-tetralone (yield: 30%).

¹H-NMR:(CDCl₃) δ: 25(m, 6H);3.05(t, 2H);3.2(t, 2H);3.3(m, 1H);3.5(m, 1H);4.25(m, 2H);4.7–4.9(m, 3H);5.3(d, 1H);5.4–5.55(m, 2H);5.95(m, 1H);7.05(d, 1H);7.15(t, 1H);7.2–7.35(m, 1H);7.4(d, 1H);7.5(d, 1H);7.75(d, 1H);8.0(s, 1H).

EXAMPLE 20

(1S,5R,6S,8R)-6-(1-Hydroxyethyl)-1-methyl-2-(2-(2-oxo-butyl)-1-indanone-4-yloxymethyl)carbapenem-3-carboxylic acid sodium salt The title compound was prepared from allyl (1S,5R,6S,8R)-6-(1-hydroxyethyl)-1-methyl- 2-(2-(2-oxo-butyl)-1-inandone-4-yloxymethyl)carbapenem-3-carboxylate using a similar method to that described in Example 1 (yield: 32%).

¹H-NMR: (DMSO-d₆+AcOD) δ: 0.95(t, 3H);1.15(d, 6H);2.5(q, 2H);2.8–3.3(m, 5H);3.95(m, 1H);4.1(m, 1H);4.9(dd, 1H);5.55(d, 1H); 7.25(m, 2H);7.4(m, 1H).

The starting material was prepared as follows:

6-Hydroxy-2-methylene-1-indanone was prepared using a similar method to that described in Example 16 but using 6-hydroxy-1-indanone instead of 4-hydroxy-1-indanone. To the above compound (0.3 g; 1.87 mmol) in suspension in ethanol, were added, at ambient temperature, under argon: propionaldehyde (0.27 ml; 3.75 mmol), triethylamine (80 μl; 0.56 mmol) and 3,4-dimethyl-5-(2hydroxyethyl)thiazolium iodide (50.6 mg; 0.18 mmol). The mixture was heated at 80° C. for 17 hours. The solution was taken up in CH₂Cl₂ and washed in water and a saturated solution of NaCl. The organic phase was dried over MgSO₄, filtered and evaporated. The residue was purified by flash chromatography on silica gel, eluting with petroleum ether/ethyl acetate (7/3), to give 2-(2-oxobutyl)-4-hydroxy-1-indanone (0.28 g; 70%).

¹H-NMR: (DMSO-d₆) δ: 0.9(t, 3H);2.45–3.0(m, 6H);3.15(m, 1H);7.05(d, 1H);7.1(m, 1H);7.25(d, 1H);9.8(s, 1H).

Allyl (1S,5R,6S,8R)-1-methyl-2-(2-(2-oxo-butyl)-1-indanone-4-yloxymethyl)-6-(1-(tertbutyldimethylsilyloxy) ethyl)carbapenem-3carboxylate was prepared using a similar method to that described in example 5 but using the compound above instead of 6-hydroxychromone (yield: 50%).

¹H-NMR (CDCl₃) δ: 0(s, 6H);0.9(s, 9H);1.1(m, 3H);1.25(m, 6H);2.5(m, 2H);2.6(dd, 1H);2.7(m, 2H);3.0(m, 1H);3.15(dd, 1H);3.3(m, 1H);3.45 1H);4.25(m, 2H);4.7–4.9(m, 3H);5.3(d, 1H);5.45(d, 1H);5.55 (d, 1H);5.95(m, 1H),7.05–7.4(m, 3H).

Using the above compound allyl (1S,5R,6S,8R)-6-(1-hydroxyethyl)-1-methyl-2-(2-(2-oxo-butyl)-1-indanone-4-yloxymethyl) carbapenem-3-carboxylate was prepared using a similar method to that described in Example 5 (yield: 67%).

¹H-NMR: (DMSO-d₆) δ: 1.1 (t, 3H);1.25(d, 3H);1.35(d, 3H);2.5(q, 2H); 2.6(dd, 1H);2.7(s, 2H);3.05(m, 1H);3.15(dd, 1H);3.35(m, 1H);3.45(m, 1H);4.3(m, 2H);4.7–4.9(m, 3H);5.3(d, 1H);5.45(d, 1H);5.55(d, 1H);6.0(m, 1H);7.0–7.4(m, 3H).

EXAMPLE 21

(1S,5R,6S,8R)-6-(1-Hydroxyethyl)-1-methyl-2-(2-(4-pyridylmethylene)-1-tetralone-5-yloxymethyl)carbapenem-3-carboxylic acid sodium salt The title compound was prepared from allyl (1S,5R,6S,8R)-6-(1-hydroxyethyl)-1-methyl-2-(2-(4-pyridylmethylene)-1 -tetralone-5-yloxymethyl)carbapenem-3-carboxylate using a similar method to that described in Example 1 (yield: 52%).

¹H-NMR:(DMSO-d₆+AcOD) δ: 1,15(m, 6H);2.95(t, 2H);3.1(t, 2H);3.15–3.25(m, 2H);3.95(m, 1H);4.05(dd, 1H);4.8(d, 1H);5.5(d, 1H);7.3(d, 1H);7.35(t, 1H);7.5(d, 2H);7.6(m, 2H);8.7(s, 2H).

The starting material was prepared as follows:

A mixture of 5-methoxy-1-tetralone (0.1 g; 0.56 mmol), pyridine-4-carboxaldehyde (91 μl ; 0.85 mmol), piperidine (16.8 μl; 0.17 mmol) and acetic acid (9.7μl ; 0.17 mmol) was heated at 130° C. for one hour. The mixture was taken up in CH₂Cl₂ and washed in water and in a saturated aqueous solution of NaCl. The organic phase was dried over MgSO₄, filtered and evaporated. The residue was purified by flash chromatography on silica gel, eluting with CH₂Cl₂/CH₃CN (7/3) to give 5-methoxy-2-(4-pyridylmethylene)-1-tetralone (74 mg; 52%).

¹H-NMR:(CDCl₃) δ: 2.95(t, 2H);3.05(t, 2H);3.9(s, 3H);7.05(d, 1H);7.25–7.4(m, 2H);7.7(d, 1H);7.75(d, 1H);8.65(d, 2H).

To a solution of the above compound (560 mg; 2.13 mmol) in CH₂Cl₂ was added, dropwise at –65° C. and under argon, boron tribromide (1.05 ml 11.15 mmol). After 30 minutes the mixture was brought up to 0° C. and then left to come back to the ambient temperature. After two and a half hours the mixture was mixed in methanol, concentrated to dryness, then taken up in CH₂Cl₂ and washed in water. The aqueous phase was neutralised to pH 7 using a dilute solution of NaHCO₃ and the compound was extracted in CH₂C₂. The organic phase was dried over MgSO₄, filtered and evaporated to give 5-hydroxy-2-(4-pyridylmethylene)-1-tetralone (200 mg; 40%).

¹H-NMR:(DMSO-d₆) δ: 2.8(t, 2h);3.05(t, 2H);7.1(d, 1H);7.25(t, 1H);7.45(m, 2H);7.55(s, 1H);8.65(d, 2H);9.9(s, 1H).

Allyl (1S,5R,6S,8R)-1-methyl-2-(2-(4-pyridylmethylene)-1-tetralone-5-yloxymethyl)-6-(1-(tertbutyldimethylsilyloxy)ethyl) carbapenem-3-carboxylate was prepared using a similar method to that described in Example 5 but using 5-hydroxy-2-(4-pyridylmethylene)-1-tetralone instead of 6-hydroxychromone (yield: 65%).

¹H-NMR:(CDCl₃) δ:0(s, 6H);1.0(s, 9H);1.35(d, 3H);1.4(d, 3H);3.05(t, 2H);3.15(t, 2H);3.35(m, 1H);3.5(m, 1H);4.35(m, 2H);4.8–4.95(m, 3H);5.35(d, 1H);5.5–5.65(m, 2H);6.05(m, 1H);7.2(d, 1H);7.35–7.45(m 3H);7.8(s, 1H);7.9(d, 1H);8.75(d, 2H).

Using the above compound, allyl (1S,5R,6S,8R)-6-(1-hydroxyethyl)-1-methyl-2-(2-(4-pyridylmethylene)-1-tetralone-5-yloxymethyl)carbapenem-3-carboxylate was prepared using a similar method to that described in Example 5(yield: 71%).

¹H-NMR:(CDCl₃) δ: 25(m, 6H);1.65(s, 1H);2.95(t, 2H);3.05(m, 2H);3.3(m, 1H);3.45(m, 1H);4.25(m, 2H);4.7–4.9(m, 3H);5.3(d, 1H);5.45(d, 1H);5.5(d, 1H);5.95(m, 1H);7.05(d, 1H);7.25–7.35(m, 3H);7.7(s, 1H);7.8(d, 1H);8.7(d, 2H).

EXAMPLE 22

(1S,5R,6S,8R)-6-(1-Hydroxyethyl)-1-methyl-2-(2-(3-pyridyl)-1-tetralone-6-yloxymethyl)carbapenem-3-carboxylic acid sodium salt The title compound was prepared from allyl (1S,5R,6S, 8R)-6-(1-hydroxyethyl)-1-methyl-2-(2-(3-pyridyl)-1-tetralone-6-yloxymethyl)carbapenem-3-carboxylate using a similar method to that described in Example 1 (yield: 42%).

¹H-NMR: (DMSO-d₆) δ: 1.14(d, 6H); 2.21–2.31(m, 1H); 2.4–2.48(m, 1H), 2.95–3.02(m, 1H); 3.11–3.2(m, 1H); 3.25–3.32(m, 2H); 3.91–4.02(m, 2H); 4.12(dd, 1H); 4.87(d, 1H); 5.62(d, 1H); 6.9–7.0(m, 2H); 7.32–7.41(m, 1H); 7.6–7.67(m, 1H); 7.91(d, 1H); 8.4–8.51(m, 2H).

The starting material was prepared as follows:

To a suspension of 6-methoxy-2-(3-pyridyl)-1-tetralone (288 mg; 1.1 mmol) in CH₂Cl₂ (10 ml) was added, at 0° C. under argon, boron tribromide (215 μl; 2.2 mmol). It was left for 10 minutes and then, water, ethyl acetate and 2N NaHCO₃ were added to bring the mixture to pH 9.5. The mixture was then acidified to pH 7–8 with 2N HCl and then extracted three times with ethyl acetate. The organic phase was washed with water and a saturated aqueous solution of NaCl , dried over MgSO₄ filtered and evaporated. The residue was subjected to chromatography using a silica column, eluting with petroleum ether/ethyl acetate (1/9), to give 6-hydroxy-2-(3-pyridyl)-1-tetralone (208 mg; 79%) as a yellow solid.

¹H-NMR: (CDCl₃) δ: 2.15–2.27(m, 1H); 2.3–2.41(m, 1H); 2.85–2.93(m, 1H); 3.02–3.14(m, 1H); 3.87–3.95(dd, 1H); 6.7(d, 1H); 6.75(dd, 1H); 7.32–7.35(m, 1H); 7.58–7.61(m, 1H) 1 7.78(d, 1H) 1 8.42(d, 1H); 8.45(dd, 1H); 10.42(s, 1H).

Using the above compound, instead of 6-hydroxychromone, allyl (1S,5R,6S,8R)-1-methyl-2-(2-(3-pyridyl)-1-tetralone-6-yloxymethyl)-6-(1-(tertbutyldimethylsilyloxy)ethyl)carbapenem-3carboxylate was prepared using a similar method to that described in Example 5.

¹H-NMR: (CDCl₃) δ: 0.08(s, 6H); 0.88(s, 9H); 1.22–1.26(m, 6H); 2.38–2.42(m, 2H); 2.99–3.03(m, 1H); 3.10–3.15(m, 1H); 3.26(dd, 1H); 3.4–3.43(m, 1H); 3.73–3.79(m, 1H); 4.2–4.24(m, 2H); 4.7–4.83(m, 3H); 5.25–5.3(m, 1H); 5.41–5.5(m, 1H); 5.51–5.58(m, 1H); 5.9–6.0(m, 1H); 6.8(d, 1H); 6.89(dd, 1H); 7.4–7.7(m, 2H); 8.04(d, 1H); 8.46(d, 1H); 8.5(dd, 1H).

Using the above compound, allyl (1S,5R,6S,8R)-6(1-hydroxyethyl)-1-methyl-2-(2-(3-pyridyl)-1-tetralone-6-yloxymethyl)carbapenem-3-carboxylate was prepared using a similar method to that described in Example 5 (yield =54%).

¹H-NMR (CDCl₃) δ: 1.22–1.29(m, 3H); 1.34(d, 3H); 2.36(m, 2H); 2.98–3.03(m, 1H); 3.07–3.18(m, 1H); 3.3(dd, 1H); 3.4–3.5(m, 1H); 3.74–3.81(m, 1H); 4.21–4.3(m, 2H); 4.7–4.89(m, 3H); 5.3(dd, 1H); 5.47(dd, 1H); 5.55(d, 1H); 5.91–6.05(m, 1H) 6.75(d, 1H); 6.88(dd, 1H); 7.26–7.3(m, 1H); 7.61–7.7(m, 1H); 8.05(d, 1H); 8.5(d, 1H); 8.51–8.55(m, 1H).

EXAMPLE 23

(1S,5R,6S,8R)-2-(2-(Dimethylamino)chromone-6-yloxymethyl)-6-(1-hydroxyethyl)-1-methylcarbapenem-3-carboxylic acid sodium salt The title compound was prepared from allyl (1S,5R,6S, 8R)-2-(2-(dimethylamino)chromone- 6-yloxymethyl)-6-(1-hydroxyethyl)-1-methylcarbapenem-3-carboxylate using a similar method to that described in Example 1 (yield 54.3%).

¹H-NMR: (DMSOd₆+AcOD) δ: 1.05–1.2 (m, 6H); 3.08(s, 6H); 3.17–3.3(m, 2H); 3.9–4.0(m, 1H); 4.08(dd, 1H); 4.82(d, 1H); 5.32(s, 1H); 5.48(d, 1H); 7.25(dd, 1H); 7.38(d, 1H); 7.46(d, 1H).

The starting material was prepared as follows:

To a solution of 2-hydroxy-5-methoxyphenyl methyl ketone (10 g; 60 mmol) in ether (120 ml) was added, dropwise, boron trifluoride etherate (7.4 ml; 60 mmol). After one hour at ambient temperature the precipitate was filtered, washed with ether and dried under reduced pressure to give (2-acetyl-4-methoxyphenolato)difluoroboron(1+) fluoride (10 g; 71.4%).

$^1$H-NMR: (CDCl$_3$) δ: 2.85 (s, 3H); 3.85(s, 3H); 6.96(d, 1H); 7.1(d, 1H); 7.48(dd, 1H).

A suspension of the above compound (5 g; 21.5 mmol) in dichloroethane (100 ml) and N,N-dimethyldichloromethyleniminium chloride (3.5 g; 21.5 mmol) was heated at 80° C. for 3 hours. After cooling to ambient temperature, the solid was filtered, washed with cold dichloroethane and cold ether, then dried under reduced pressure. The solid was taken up into CH$_3$CN (75 ml) and water (7.8 ml) and the mixture was heated at 50° C. for 30 minutes. After evaporation, a solution of NaHCO$_3$ was poured over the product and it was extracted with ethyl acetate. The organic phase was washed with a saturated aqueous solution of NaCl, dried over MgSO$_4$ and evaporated to give 2-(dimethylamino)-6-methoxychromone as a beige solid (2.7 g; 57.4%).

$^1$H-NMR: (CDCl$_3$) δ: 3.1 (s, 6H); 3.89(s, 3H); 5.42(s, 1H); 7.11(dd, 1H); 7.23(d, 1H); 7.6(d, 1H).

To a solution of the above compound (1.5 g; 6.8 mmol) in CH$_2$Cl$_2$ (70 ml) at −70° C., was slowly added boron tribromide (3.2 ml; 34 mmol). The mixture was left at −70° C. for 40 minutes, then at 0° C. for 30 minutes and finally at ambient temperature for 1 hour and 30 minutes. After evaporation the residue was poured over ice, the mixture was taken to pH 9.2 using a dilute solution of NaOH and the resulting precipitate was filtered off, washed with water and dried under reduced pressure to give 2-(dimethylamino)-6-hydroxychromone (1.2 g; 85%).

$^1$H-NMR: (DMSO-d$_6$) δ: 3.05(s6H); 5.24(s, 1H); 7.03(dd, 1H); 7.22(d, 1H); 7.33(d, 1H); 9.7(s, 1H).

Using the above compound instead of 6-hydroxychromone, allyl (1S,5R,6S,8R)-2-(2-(dimethylamino)chromone-6-yloxymethyl)-1-methyl-6-(1-(tertbutyldimethylsilyloxy)ethyl)carbapenem-3carboxylate was prepared using a similar method to that described in Example 5 (yield: 65%).

$^1$H-NMR: (CDCl$_3$) δ: 0.1 (s, 6H); 0.9(s, 9H); 1.23(d, 3H); 3.12(s, 6H); 4.7–4.86(m, 3H); 5.23–5.5(3H); 5.42(s, 1H); 5.9–6.02(m, 1H); 7.15(dd, 1H); 7.41–7.56(m, 2H).

Using the above compound allyl (1S,5R,6S,8R)-2-(2-(dimethylamino)chromone-6-yloxymethyl)-6-(1-hydroxyethyl-1-methylcarbapenem-3-carboxylate was prepared using a that described in Example 5.

$^1$H-NMR: (CDCl$_3$) δ: 1.25 (d, 3H); 1.35(d, 3H); 3.12(s, 6H); 3.31(dd, 1H); 3.42–3.52(m, 1H); 4.2–4.28(m, 2H); 4.68–4.88(m, 3H); 5.25–5.51(m, 3H); 5.42(s, 1H); 5.91–6.05(m, 1H); 7.12(dd, 1H); 7.4–7.58(m, 2H).

EXAMPLE 24

(1S,5R,6S,8R)-6-(1-Hydroxyethyl)-1-methyl-2-(2-(morpholino) chromone-6-yloxymethyl)carbapenem-3-carboxylic acid sodium salt The title compound was prepared from allyl (1S,5R,6S,8R)-6-(1-hydroxyethyl)-1-methyl-2-(2-(morpholino)chromone-6-yloxymethyl)carbapenem-3-carboxylate using a similar method to that described in Example 1 (yield: 37.2%).

$^1$H-NMR (DMSO-d$_6$+AcOD) δ: 1.07–1.20(m, 6H); 3.2–3.3(m, 2H); 3.43–3.57(m, 4H); 3.65–3.8(m, 4H); 3.91–4.0(m, 1H); 4.1(dd, 1H); 4.83(d, 1H); 5.45(d, 1H); 5.53(s, 2H); 7.28(dd, 1H); 7.4(d, 1H); 7.48(d, 1H).

The starting material was prepared as follows:

A suspension of (2-acetyl-4-methoxyphenolato) difluoroboron(1+) fluoride (5 g; 21.5 mmol) in CH$_2$Cl$_2$ (100 ml) and 4-(dichloromethylene)morpholinium chloride (4.4 g; 21.5 mmol) was heated at 80° C. for 3 hours. After cooling to ambient temperature the solid was filtered off washed with cold CH$_2$Cl$_2$ and cold ether and dried under reduced pressure. The solid was taken up in CH$_3$CN (75 ml) and water (8 ml) and the mixture was heated at 50° C. for 30 minutes. After evaporation a solution of NaHCO$_3$ was poured over the product. After extraction with CH$_2$Cl$_2$ the organic phase was washed with a saturated aqueous solution of NaCl, dried over MgSO$_4$ and evaporated to give 6-methoxy-2-(morpholino)chromone as a solid (2.5 g;

$^1$H-NMR: (CDCl$_3$) 8:3.5 (t, 4H); 3.83(t, 4H); 3.88(s, 3H); 5.5(s,1H); 7.13(dd, 1H); 7.23(d, 1H); 7.57(d, 1H).

To a solution of the above compound (1.5 g; 5.7 mmol) in CH$_2$Cl$_2$ (70 ml) at −70° C. was slowly added boron tribromide (2.7 ml; 28.5 mmol). The mixture was left for 30 minutes at −70° C., then for 40 minutes at 0° C. and finally for 2 hours at ambient temperature. After evaporation the residue was poured over ice, the mixture was taken to pH 7.8 using a dilute solution of NaHCO$_3$, then neutralised to pH 7.0, the precipitate was filtered, washed with water and dried in a vacuum to give 6-hydroxy-2-(morpholino)chromone (1 g; 71.5%).

$^1$H-NMR: (DMSO-d$_6$) δ: 3.43–3.52 (m, 4H); 3.67–3.75(m, 4H); 5.45(s, 1H); 7.05(dd, 1H); 7.22(d, 1H); 7.35(d, 1H); 9.73(s, 1H).

Using the above compound instead of 6-hydroxychromone, allyl (1S,5R,6S,8R)-1-methyl-2-(2-(morpholino)chromone-6-yloxymethyl)-6-(1-(tertbutyldimethylsilyloxy)ethyl)carbapenem-3-carboxylate was prepared using a similar method to that described in Example 5.

$^1$H-NMR: (CDCl$_3$) δ: 0.1 (s, 6H); 0.92(s, 9H); 1.2–1.3(m, 6H); 3.38(dd, 1H); 3.4–3.56(m, 1H); 3.52(t, 4H); 3.85(t, 4H); 4.2–4.3(m, 2H); 4.7–4.88(m, 3H); 5.25–5.5(m, 4H); 5.92–6.05(m, 1H); 7.17(dd, 1H); 7.3(d, 1H); 7.7(d, 1H).

Using the above compound allyl (1S,5R,6S,8R)-6-(1-hydroxyethyl)-1-methyl-2-(2-(morpholino)chromone-6-yloxymethyl)carbapenem-3-carboxylate was prepared using a similar method to that described in Example 5.

$^1$H-NMR: (CDCl$_3$) 4:1.25 (d, 3H); 1.35(d, 3H); 3.31(dd, 1H); 3.42–3.55(m, 5H); 3.8–3.87(m, 4H); 4.2–4.27(m, 2H); 4.7–4.9(m, 3H); 5.25–5.52(m, 4H); 5.92–6.05(m, 1H); 7.15(dd, 1H); 7.35(d, 1H); 7.65(d, 1H).

EXAMPLE 25

(1S,5R,6S,8R)-6-(1-Hydroxyethyl)-1-methyl-2-(3-(phenylaminomethyl)-chromone-6-ylthiomethyl)carbapenem-3-carboxylic acid sodium salt The title compound was prepared from allyl (1S,5R,6S, 8R)-6-(1-hydroxyethyl)-1-methyl-2-(3-(phenylaminomethyl)-chromone-6-ylthiomethyl)carbapenem-3-carboxylate using a similar method to that described in Example 1 (yield: 17%).

¹H-NMR: (DMSO-d₆+AcOD) δ: 1.03–1.17(m, 6H); 3.2(dd, 1H); 3.25–3.35(m, 1H); 3.72(d, 1H); 3.89–3.99(m, 1H); 4.04(dd, 1H); 4.10(s, 2H); 4.76(d, 1H); 6.58(t, 1H); 6.64(d, 2H); 7.07(t, 2H); 7.6(d, 1H); 7.76(dd, 1H); 8.02(d, 1H); 8.25(s, 1H).

The starting material was prepared as follows:

A suspension of 6-bromo-3-formylchromone (150 mg; 0.59 mmol) in toluene (10 ml) was heated at 50°–55° C. until the solute had completely dissolved. Aniline (55 µl; 0.59 mmol) was added and the temperature was maintained for 15 minutes. On cooling, a yellow precipitate formed which was filtered off and dried under reduced pressure to give 6-bromo-3-(phenyliminomethyl)chromone (190 mg; 98%).

The above compound (1.9 g; 5.8 mmol) was mixed with CH₃CN (50 ml) and methanol (60 ml) and heated at 40° C. until it had all dissolved. The mixture was cooled to 25°–30° C., acetic acid (1.65 ml; 29 mmol) was added followed by sodium cyanoborohydride (436 mg; 7 mmol). The mixture was stirred at ambient temperature for 15 minutes, 12N HCl (0.966 ml; 11.6 mmol) was added, it was stirred for a further 15 minutes at ambient temperature and evaporated. The residue was taken up in water, neutralised with a dilute aqueous solution of NaHCO₃ and extracted with ethyl acetate. After washing, drying over MgSO₄ and evaporation, the product was purified by flash chromatography, eluting with ethyl acetate/petroleum ether (25/75) to give 6-bromo-3-(phenylaminomethyl)chromone as yellow crystals (920 mg 50%).

¹H-NMR: (CDCl₃) δ: 4.23–4.34(m, 3H); 6.65(d, 2H); 6.75(t, 1H); 7.18(t, 2H); 7.34(d, 1H); 7.74(dd, 1H); 7.9(s, 1H); 8.35(d, 1H).

To a solution of the above compound (500 mg; 1.5 mmol) in benzene (20 ml) was added, under argon, tetrakis(triphenylphosphine) palladium (50 mg; 0.04 mmol). The mixture was heated at 85°–90° C. for 10 minutes, cooled to 50° C. and a solution of sodium triisopropylsulfidosilane (321 mg; 1.5 mmol) in anhydrous THF (3.5 ml) was added. The mixture was refluxed for 90 minutes, poured into water and extracted with ethyl acetate. The organic phase was washed with water and a saturated aqueous solution of NaCl, dried over MgSO₄, evaporated and purified by flash chromatography, eluting with ethyl acetate/petroleum ether (25/75) to give 3-(phenylaminomethyl)-6-(triisopropylsilylthio)chromone as yellow crystals (593 mg; 90%).

¹H-NMR: (CDCl₃) δ: 1.05–1.15(m, 18H); 1.2–1.32(m, 3H); 4.28(s, 2H); 4.34(br, 1H); 6.65(d, 2H); 6.73(t, 1H); 7.17(t, 2H); 7.28(d, 1H); 7.72(dd, 1H); 7.86(s, 1H); 8.32(d, 1H).

To a solution of the above compound (270 mg; 0.6 mmol) in THF (15 ml) at 0° C. was added, under argon, a solution of tetrabutylammonium fluoride in THF (1.1M; 0.56 ml; 0.6 mmol). After one hour at ambient temperature water was added. The mixture was acidified to pH 4.8 using 1N HCl and extracted with ethyl acetate. The organic phase was washed with a saturated aqueous solution of NaCl, dried over MgSO₄ and evaported to give 3-(phenylaminomethyl)chromone-6-ylthiol as a gum (170 mg; 100% unpurified) which was used immediately.

¹H-NMR: (CDCl₃) δ: 3.63(s, 1H); 4.25–4.33(m, 1H); 4.28(s, 2H); 6.65(d, 2H); 6.73(t, 1H); 7.1–7.2(m, 2H); 7.32(d, 1H); 7.53(dd, 1H); 7.9(s, 1H); 8.13(d, 1H).

Using the above compound instead of 1-indanone-6-thiol, allyl (1S,5R,6S,8R)-1-methyl-2-(3-(phenylaminomethyl)chromone-6-ylthiomethyl)-6-(1-(tertbutyldimethylsilyloxy)ethyl)carbapenem-3-carboxylate was prepared using a similar method to that described in example 17 (yield =33%).

¹H-NMR: CDCl₃ δ: 0.07 (s, 6H); 0.88(s, 9H); 1.15(d, 3H); 1.25(d, 2H); 3.2(dd, 1H); 3.3–3.4(m, 1H); 3.47(d, 1H); 4.08(dd, 1H); 4.14–4.22(m, 1H); 4.26–4.36(m, 3H); 4.58–4.74(m, 2H); 4.9(d, 1H); 5.18–5.42(m, 2H); 5.82–5.93(m, 1H); 6.65(d, 2H); 6.73(t, 1H); 7.18(t, 2H); 7.33(d, 1H); 7.63(dd, 1H); 7.88(s, 1H); 8.18(d, 1H).

Using the above compound allyl (1S,5R,6S,8R)-6-(1-hydroxyethyl)-1-methyl-2-(3-(phenylaminomethyl)chromone-6-ylthiomethyl)carbapenem-3-carboxylate was prepared using a similar method to that described in Example 17 and used in the subsequent step without further purification.

EXAMPLE 26

(1S,5R,6S,8R)-2-(2-(Acetamido)-1-tetralone-7-yloxymethyl)-6-(1-hydroxyethyl)-1-methylcarbapenem-3-carboxylic acid sodium salt The title compound was prepared from allyl (1S,5R,6S,8R)-2-(2-acetamido-1-tetralone-7-yloxymethyl)-6-(1-hydroxyethyl)-1-methylcarbapenem-3-carboxylate using a similar method to that described in Example 1 (yield 17%).

¹H-NMR: (DMSO-d₆+AcOD) δ: 1.09–1.2 (m, 6H); 1.94(s, 3H); 1.95–2.25(m, 2H); 2.88–2.97(m, 1H); 3.04–3.16(m, 1H); 3.18–3.28(m, 2H); 3.92–4.0(m, 1H); 4.03–4.11(m, 1H); 4.55–4.65(m, 1H); 4.8(d, 1H); 5.4–5.48(m, 1H); 7.21(dd, 1H); 7.31(d, 1H); 7.38(d, 1H); 8.2(d, 1H).

The starting material was prepared as follows:

A solution of 7-methoxy-1-tetralone (10 g; 56.8 mmol) in pyridine (28 ml) and hydroxylamine hyrochloride (9 g; 130.6 mmol) was refluxed for 12 hours. The mixture was poured into water and extracted with CH₂Cl₂. The organic phase was washed with 1N HCl and 0.5N NaHC₃, dried over MgSO₄ and evaporated to give 7-methoxy-,1,2,3,4-tetrahydronaphthalen-1-one oxime as a brown solid (10 g; 92.5%).

¹H-NMR: (CDCl₃) δ: 1.8–1.92(m, 2H); 2.7(t, 2H); 2.8(t, 2H); 3.83(s, 3H); 6.87(dd, 1H); 7.08(d, 1H); 7.45(d, 1H); 7.72(s, 1H).

To a solution of the above compound (11 g; 57.6 mmol) in pyridine (20 ml) at 0° C. was added, dropwise a solution of p-toluenesulfonyl chloride (11 g; 57.7 mmol) in pyridine (20 ml). The mixture was left at ambient temperature for 15 hours, then poured into water and extracted with CH₂Cl₂. The organic phase was washed with 2N HCl and 0.5N NaHC₃, dried over MgSO₄ and evaporated to give -methoxy-1-tosyloxyimino-,1,2,3,4-tetrahydronaphthalene as a brown solid (16 g; 100%).

¹H-NMR: (CDCl₃) δ: 1.75–1.87(m, 2H); 2.67(t, 2H); 2.8(t, 2H); 3.8(s, 3H); 6.91(dd, 1H); 7.07(d, 1H); 7.3–7.38(m, 3H); 7.95(d, 2H).

To a suspension of the above compound (18.6 g; 65.4 mmol) in toluene (300 ml) at 0° C. was added, under a nitrogen atomosphere, a solution of sodium methoxide (3.64 g; 67.5 mmol) in methanol (40 ml). After 24 hours at ambient temperature the precipitate was filtered off and the solution was poured into 5N HCl (400 ml). The aqueous phase was decanted and evaporated to give a brown gum. This was dissolved in warm ethanol (100 ml) and ether (150 ml) was added to give 2-amino-7-methoxy-1-tetralone hydrochloride as a precipitate (2.65 g; 18%) which was filtered off and dried.

¹H-NMR: (D₂) δ: 2.2–2.35(m, 1H); 2.52–2.64(m, 1H); 3.08–3.28(m, 2H); 3.9(s, 3H); 4.43(dd, 1H); 7.3(dd, 1H); 7.38(d, 1H); 7.53(d, 1H).

To a suspension of the above compound (1.5 g; 6.6 mmol) in CH$_2$Cl$_2$ (100 ml) were added acetyl chloride (0.5 ml; 6.6 mmol) and triethylamine (4.6 ml; 36 mmol). After 20 hours at ambient temperature the mixture was evaporated, the residue was mixed in water and extracted with ethyl acetate. The organic phase was washed with 1N HCl, with water and with a saturated aqueous solution of NACl. It was then dried and evaporated to give 2-acetamido-7-methoxy-1-tetralone as a brown solid (1 g; 66.6%).

$^1$H-NMR: (DMSO-d$_6$) δ: 1.92(s, 3H); 1.96–2.03(m, 1H); 2.14–2.25(m, 1H); 2.88–2.97(m, 1H); 3.03–3.17(m, 1H); 3.8(s, 3H); 4.53–4.63(m, 1H); 7.18(dd, 1H); 7.3(d, 1H); 7.35(d, 1H); 8.2(d, 1H).

To a solution of the above compound (1 g; 4.3 mmol) in CH$_2$Cl$_2$ (70 ml) at −70° C. was slowly added boron tribromide (2.8 ml; 30.1 mmol). After 20 minutes at −70° C., then 40 minutes at 0° C. and 3 hours at ambient temperature, the mixture was evaporated. A saturated aqueous solution of NaHCO$_3$ was poured onto the residue until the pH was 7.8. After one hour the pH was neutralised to 7.0, the precipitate was filtered, washed with water and dried to give 2-acetamido-7-hydroxy1-tetralone (260 mg; 27.6%).

$^1$H-NMR: (DMSO-d$_6$) δ: 1.96–2.03(m, 1H); 1.91(s, 3H); 2.12–2.21(m, 1H); 2.81–2.91(m, 1H); 2.98–3.11(m, 1H); 4.5–4.6(m, 1H); 7.0(dd, 1H); 7.18(d, 1H); 7.25(d, 1H); 8.15(d, 1H); 9.63(s, 1H).

Using the above compound instead of 5-hydroxy-1tetralone, allyl (1S,5R,6S,8R)-2-(2-acetamido-7-yloxymethyl)6-(1-hydroxyethyl)-1-methylcarbapenem-3-carboxylate was prepared using a similar method to that described in Example 1 (yield: 83%).

$^1$H-NMR: CDCl$_3$ δ: 1.23(d, 3H); 1.35(d, 3H); 1.8–1.83(m, 1H); 2.02–2.09(m, 1H); 2.11(s, 3H); 2.9–3.02(m, 1H); 3.12–3.27(m, 1H); 3.3(dd, 1H); 3.4–3.5(m, 1H); 4.18–4.3(m, 2H); 4.55–4.92(m, 4H); 5.25–5.55(m, 3H); 5.95–6.06(m, 1H); 6.62(b, 1H); 7.05–7.13(m, 2H); 7.2(d, 1H).

EXAMPLE 27

(1S,5R,6S,8R)-2-(3-(Dimethylaminomethyl)chromone-6-yloxymethyl)-6-(1-hydroxyethyl)-1-methylcarbapenem-3-carboxylic acid sodium salt The title compound was prepared from allyl (1S,5R,6S,8R)-2-(3-(dimethylaminomethyl)chromone-6-yloxymethyl)-6-(1-hydroxyethyl)-1-methylcarbapenem-3-carboxylate using a similar method to that described in Example 1 (yield: 25%).

$^1$H-NMR: (DMSO$_6$+AcOD) δ: 1.12–1.14(m, 6H); 2.7(s, 6H); 3.23–3.31(m, 2H); 3.90–4.03(m, 3H); 4.1(dd, 1H); 4.95(d, 1H); 5.5(d, 1H); 7.48–7.57(m, 2H); 7.72(d, 1H); 8.55(s, 1H).

The starting material was prepared as follows:

A mixture of 6-hydroxychromone (4.5 g; 27.7 mmol), CH$_2$Cl$_2$ (150 ml), water (150 ml), dimethylsulphate (4 ml; 41.5 mmol), benzyltributylammmonium bromide (2 g; 5.5 mmol) and NaHCO$_3$ (1.67 g; 41.5 mmol) was stirred for 24 hours at ambient temperature. The organic phase was decanted, washed with water, a dilute solution of ammonium hydroxide and with 1N HCl, it was dried over MgSO$_4$ and evaporated. It was purified by chromatography, eluting with ethyl acetate/petroleum ether (50/50) to give 6-methoxychromone (4 g; 83%) as a brown solid.

$^1$H-NMR: (CDCl$_3$) δ: 3.9(s, 3H); 6.33(d, 1H); 7.28(dd, 1H); 7.4(d, 1H); 7.58(d, 1H); 7.85(d, 1H).

A mixture of the above compound (1.75 g; 9.9 mmol), ethanol (10 ml), paraformaldehyde (600 mg), 3A activated sieve and dimethylamine hydrochloride (892 mg; 10.9 mmol) was refluxed for 15 hours. An excess of paraformaldehyde (300 mg) and dimethylamine hydrochloride (225 mg; 2.7 mmol) was added and the mixture heated at reflux for a further 4 hours. The precipitate was filtered and washed with ethanol. The filtrate was evaporated, put back into water, taken to pH 9 using 2N NaOH and extracted with ethyl acetate. The organic phase was dried, evaporated, then purified on silica gel, eluting with methanol/CH$_2$Cl$_2$ (20/80) to give 3-dimethylaminomethyl-6-methoxychromone (763 mg; 33%) as an oil.

$^1$H-NMR: (CDCl$_3$) δ: 2.3(s, 6H); 3.4(s, 2H); 3.9(s, 3H); 7.2(dd, 1H); 7.4(d, 1H); 7.6(d, 1H); 7.95(s, 1H).

To a solution of the above compound (750 mg; 3.42 mmol) in CH$_2$Cl$_2$ (8 ml) was added, at −70° C., boron tribromide (1.6 ml; 17.1 mmol). The mixture was left for 30 minutes at −70° C., for 2 hours at 0° C. and then at ambient temperature overnight. After concentrating the mixture under reduced pressure, the residue was taken up in water, taken to pH 9.5 with 2N NaOH and extracted with ethyl acetate. The aqueous phase was subjected to chromatography (HP20SS), eluting with water/CH$_3$CN (with a gradient of 0–50%). After concentrating the fractions, 3-dimethylaminomethyl-6-hydroxychromone (475 mg; 63.5%) was retrieved as a brown solid.

$^1$H-NMR: (DMSO-d$_6$) δ: 2.17(s, 6H); 3.75(s, 2H); 7.23(dd, 1H); 7.33(d, 1H); 7.5(d, 1H); 8.2(s, 1H).

Using the above compound allyl (1S,5R,6S,8R)-2-(3-(dimethylaminomethyl)chromone-6-yloxymethyl)-1-methyl-6-(1-(tertbutyldimethylsilyloxy)ethyl)carbapenem-3-carboxylate was prepared using a similar method to that described in Example 17 (yield: 23%).

$^1$H-NMR (CDCl$_3$) δ: 0.098 (s, 6H); 0.9(s, 9H); 1.18–1.3(m, 6H); 2.28–2.4(m, 2H); 3.05–3.15(m, 1H); 3.28(dd, 1H); 4.16–4.28(m, 2H); 4.68–4.87(m, 3H); 5.23–5.54(m, 3H); 5.9–6.05(m, 1H); 7.23–8.03(m, 4H).

Using the above compound allyl (1S,5R,6S,8R)-2-(2-(3-dimethylaminomethyl)chromone-6-yloxymethyl)-6-(1-hydroxyethyl)-1-methylcarbapenem-3-carboxylate was prepared using a similar method to that described in Example 17.

I claim:

1. A compound of the formula (I)

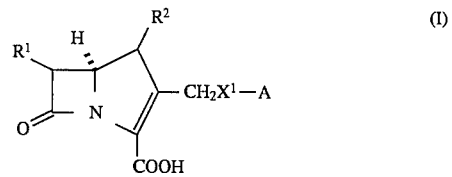

wherein

R$^1$ is hydroxymethyl, 1-hydroxyethyl or 1-fluoroethyl;

R$^2$ is hydrogen or C$_{1-4}$alkyl;

X$^1$ is oxygen or sulphur; and

A is of the formula

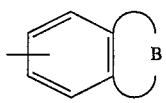

wherein

B is of the formula —$CH_2$—C(=O)—$(CH_2)_n$—, —C(=O)—$(CH_2)_{n1}$—, —C(=O)—CH=CH—$X^2$—, —C(=O)$CH_2CH_2X^2$—, —$(CH_2)_n$C(=O)NH— or —CH=CHC(=O)NH— wherein n is 1 or 2, $n^1$ is 2 or 3 and $X^2$ is NH, O or S; and wherein A optionally is substituted on one or more ring carbon atoms with one or more substituents selected from groups a) and b) consisting of:

a) $C_{1-}$alkanoyl; hydroxy $C_{1-2}$alkyl; cyano; carbamoyl; $C_{1-4}$alkycarbamoyl; di-$C_{1-4}$alkycarbamoyl; $C_{1-4}$alkyls(O)$_p$-where p is 1 or 2; aminosulphonyl; $C_{1-4}$alkylaminosulphonyl; di-$C_{1-4}$alkylaminosulphonyl; amino$C_{1-2}$alkyl; $C_{1-4}$alkylamino$C_{1-2}$alkyl; di-$C_{1-4}$alkylamino$C_{1-2}$alkyl; hydroxyiminomethyl; $C_{1-4}$alkoxyiminomethyl; $C_{1-4}$alkanesulphonamido; (N-$C_{1-4}$alkyl)-$C_{1-4}$alkanesuphonamido; $C_{1-2}$alkyl substituted by N-imidazole, optionally substituted on a ring carbon by amino, and wherein the imidazole ring is linked via a ring nitrogen; $C_{1-4}$alkylamino; di-$C_{1-4}$alkylamino; $C_{1-4}$alkanoylamino; and thienyl$C_{1-2}$alkylene; and b) $C_{1-4}$alkylthio; $C_{1-4}$alkyl; amino; benzoyl; benzoyl$C_{1-2}$alkyl; 2-oxo$C_{3-4}$alkyl; phenylamino$C_{1-2}$alkyl; morpholino; pyridyl$C_{1-2}$alkylene; halo; nitro; hydroxy; $C_{1-4}$alkoxy; $C_{1-4}$alkoxycarbonyl; carboxy; sulphonic acid; and trifluoromethyl;

or a pharmaceutically acceptable salt or an in vivo hydrolysable ester thereof.

2. The compound according to claim 1 wherein $R^1$ is 1-hydroxyethyl.

3. The compound according to claim 1 wherein $R^2$ is hydrogen or methyl.

4. The compound according to claim 1 wherein $R^2$ is methyl.

5. The compound according to claim 1 in which A is substituted on at least one ring carbon atom by at least one substituent selected from group a).

6. The compound according to claim 1 in which A is substituted on one or more ring carbon atoms by 1 or 2 substituents selected from groups a) and b).

7. The compound according to claim 1 in which A is substituted on one or more ring carbon atoms by hydroxymethyl, carbamoyl, thienylmethylene, dimethylaminomethyl, or dimethylamino.

8. The compound according to claim 1 in which ring B of A is substituted.

9. The compound according to claim 1 wherein B is of the formula —C(=O)$CH_2CH_2$—, —C(=O)$CH_2CH_2CH_2$—, —C(=O)CH=CH—O—, —C(=O)$CH_2CH_2$O—, —NHC(=O)$CH_2$—, —NHC(=O)$CH_2CH_2$— or —C(=O)$CH_2CH_2$S—.

10. The compound according to claim 1 of the formula (II):

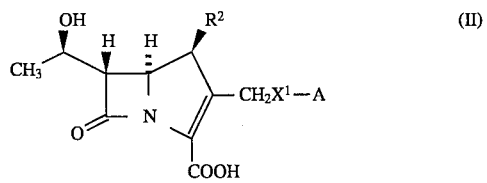

wherein $R^2$, $X^1$ and A are as defined in claim 1.

11. The compound according to claim 1 which is (1S,5R,6S,8R)-6-(1-hydroxyethyl)-1-methyl-2-(1-tetralone-5-yloxymethyl)carbapenem-3-carboxylic acid, (1S,5R,6S,8R)-6-(1-hydroxyethyl)-1-methyl-2-(1-tetralone-7-yloxymethyl)carbapenem-3-carboxylic acid, (1S,5R,6S,8R)-6-(1-hydroxyethyl)-2-(1-indanone-5-ylthiomethyl)-1-methylcarbapenem-3-carboxylic acid, (1S,5R,6S,8R)-2-(4-chromanone-7-ylthiomethyl)-6-(1-hydroxyethyl)-1-methylcarbapenem-3-carboxylic acid, (1S,5R,6S,8R)-2-(chromone-6-yloxymethyl)-6-(1-hydroxyethyl)-1-methylcarbapenem-3carboxylic acid, (1S,5R,6S,8R)-6-(1-hydroxyethyl)-2-(1-indanone-5-yloxy-methyl)-1-methylcarbapenem-3-carboxylic acid, (1S,5R,6S,8R)-6-(1-hydroxyethyl)-2-(2-hydroxymethyl-2-methyl-4-chromanone-6-yloxymethyl)-1-methylcarbapenem-3-carboxylic acid, (1S,5R,6S,8R)-6-(1-hydroxyethyl)-1-methyl-2-(1-tetralone-7-ylthiomethyl)carbapenem-3-carboxylic acid, (1S,5R,6S,8R)-6-(1-hydroxyethyl)-1-methyl-2-(1-tetralone-6-ylthiomethyl)carbapenem-3-carboxylic acid, (1S,5R,6S,8R)-6-(1-hydroxyethyl)-1-methyl-2-(1-tetralone-6-yloxymethyl)carbapenem-3-carboxylic acid, (1S,5R,6S,8R)-2-(4-chromanone-7-yloxymethyl)-6-(1-hydroxyethyl)-1-methylcarbapenem-3-carboxylic acid, (1S,5R,6S,8R)-6-(1-hydroxyethyl)-1-methyl-2-(1-methyl indolin-2-one-5-ylthiomethyl)carbapenem-3-carboxylic acid, (1S,5R,6S,8R)-6-(1-hydroxyethyl)-1-methyl-2-(2-oxo-1,2,3,4-tetrahydroquinolin-6-ylthiomethyl)carbapenem-3-carboxylic acid, (1S,5R,6S,8R)-6-(1-hydroxyethyl)-1-methyl-2-(1-methyl-2-oxo-1,2,3,4-tetrahydroquinolin-6-ylthiomethyl)carbapenem-3carboxylic acid, (1S,5R,6S,8R)-6-(1-hydroxyethyl)-1-methyl-2-(4-thiochromanone-7-ylthiomethyl)carbapenem-3-carboxylic acid, (1S,5R,6S,8R)-2-((2-benzoylmethyl)-1-indanone-4-yloxymethyl)-6-(1-hydroxyethyl)-1-methylcarbapenem-3-carboxylic acid, (1S,5R,6S,8R)-6-(1-hydroxyethyl)-2-(1-indanone-6-ylthiomethyl)-1-methylcarbapenem-3-carboxylic acid, (1S,5R,6S,8R)-6-(1-hydroxyethyl)-1-methyl-2-(2-(2-thienylmethylene)-1-indanone-4-yloxymethyl)carbapenem-3-carboxylic acid, (1S,5R,6S,8R)-6-(1-hydroxyethyl)-1-methyl-2-(2-(2-thienylmethylene)-1-tetralone-5-yloxymethyl)carbapenem-3-carboxylic acid, (1S,5R,6S,8R)-6-(1-hydroxyethyl)-1-methyl-2-(2-(2-oxo-butyl)-1-indanone-4-yloxymethyl)carbapenem-3-carboxylic acid, (1S,5R,6S,8R)-6-(1-hydroxyethyl)-1-methyl-2-(2-(4-pyridylmethylene)-1-tetralone-5-yloxymethyl)carbapenem-3-carboxylic acid, (1S,5R,6S,8R)-6-(1-hydroxyethyl)-1-methyl-2-(2-(3-pyridyl)-1-tetralone-6-yloxymethyl)carbapenem-3-carboxylic acid, (1S,5R,6S,8R)-2-(2-(dimethylamino)chromone-6-yloxymethyl)-6-(1-hydroxyethyl)-1-methylcarbapenem-3-carboxylic acid, (1S,5R,6S,8R)-6-(1-hydroxyethyl)-1-methyl-2-(2-(morpholino) chromone-6-yloxymethyl)carbapenem-3-carboxylic acid, (1S,5R,6S,8R)-6-(1-hydroxyethyl)-1-methyl-2-(3-(phenylaminomethyl)-chromone-6-ylthiomethyl)carbapenem-3-carboxylic acid, (1S,5R,6S,8R)-2-(2-(acetamido)-1-tetralone-7-yloxymethyl)-6-(1-hydroxy ethyl)-1-methylcarbapenem-3-carboxylic acid, or (1S,5R,6S,8R)-2-(3-(dimethylaminomethyl)chromone-6-yloxymethyl)-6-(1-hydroxyethyl)-1-methylcarbapenem-3-carboxylic acid, or a pharmaceutically acceptable salt or an in vivo hydrolysable ester thereof.

12. The compound according to claim 11 wherein ring B of A is substituted on a ring nitrogen atom with a substituent selected from groups $a^1$) and $b^1$) consisting of:

$a^1$) bromo$C_{1-4}$alkyl; hydroxy$C_{1-4}$alkyl; cyanco$C_{1-4}$alkyl; carbamoyl$C_{1-4}$alkyl;

$R^a$-(CH$_2$)n", wherein $R^a$ is a 5- or 6- membered heteroayl ring having one or two ring nitrogens as the heteroatoms and n" is 1–4; and $R^bS(CH_2)$n"-wherein n" is as hereinabove defined and $R^b$ $^c_{1-4}$alkyl or a 5- or 6- membered heteroaryl ring having one or two ring nitrogens as the heteroatoms; and $b^1$) $C_{1-4}$alkyl; $C_{1-4}$alkenyl; $C_{1-4}$alkanoyl; benzoyl; and pyridoyl;

wherein any phenyl or heteroaryl group in a substituent on a ring nitrogen atom in A optionally is substituted with a group selected from hydroxy, halo, $c_{1-4}$alkyl, nitro, amino, carbamoyl, cyano and trifluoromethyl.

13. The compound according claim 12 in which a ring nitrogen atom in ring B of A is substituted by a substituent selected from group $a^1$).

14. A pharmaceutical composition which comprises an antibacterially effective amount of the compound according to claim 1 and a pharmaceutically acceptable carrier.

15. A method of treatment of a bacterial infection by administering an antibacterially effective amount of the compound of the formula (I), as defined in claim 1, to a patient in need thereof.

16. A compound of formula (III)

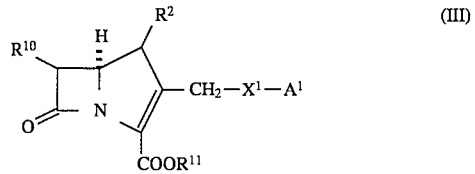
(III)

wherein $R^2$ is hydrogen or $C_{1-4}$alkyl;

$R^{10}$ is hydroxymethyl, 1-hydroxyethyl, 1-fluoroethyl, protected 1-hydroxy or protected hydroxymethyl;

$COOR^{11}$ is a carboxy or protected carboxy;

$X^1$ is oxygen or sulphur; and $A^1$ is one of the formula

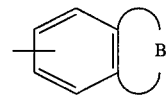

wherein

B is of the formula —CH$_2$—C(=O)—(CH$_2$)$_n$—, —C(=O)—(CH$_2$)$_{n1}$—, —C(=O)—CH=CH—X$^2$—, —C(=O)CH$_2$CH$_2$X$^2$—, —(CH$_2$)$_n$C(=O)NH— or —CH=CHC(=O)NH— wherein n is 1 or 2, n$^1$ is 2 or 3 and X$^2$ is NH, O or S; wherein A optionally may be substituted on one or more ring carbon atoms with one or more substituents selected from groups a) and b) consisting of:

a) $C_{1-4}$alkanoyl; hydroxy $C_{1-2}$alkyl; cyano; carbamoyl; $C_{1-4}$alkylcarbamoyl; di-$C_{1-4}$alkylcarbamoyl; $C_{1-4}$alkyls(O)$_p$- where p is 1 or 2; aminosulphonyl; $C_{1-4}$alkylaminosulphonyl; di-$C_{1-4}$alkylaminosulphonyl; amino$C_{1-2}$alkyl; $C_{1-4}$alkylamino$C_{1-2}$alkyl; di-$C_{1-4}$alkylamino$C_{1-2}$alkyl; hydroxyiminomethyl; $C_{1-4}$alkoxyiminomethyl; $C_{1-4}$alkanesulphonamido; (N-$C_{1-4}$alkyl)-$C_{1-4}$alkanesulphonamido; $C_{1-2}$ alkyl substituted by N-imidazole, optionally substituted on a ring carbon by amino, and wherein the imidazole ring is linked via a ring nitrogen; $C_{1-4}$alkylamino; di-$C_{1-4}$alkylamino; $C_{1-4}$alkanoylamino; and thienyl$C_{1-2}$alkylene; and b) $C_{1-4}$alkylthio; $C_{1-4}$alkyl; amino; benzoyl; benzoyl$C_{1-2}$alkyl; 2-oxo$C_{3-4}$alkyl; phenylamino$C_{1-2}$alkyl; morpholino; pyridyl$C_{1-2}$alkylene; halo; nitro; hydroxy; $C_{1-4}$alkoxy; $C_{1-4}$alkoxycarbonyl; carboxy; sulphonic acid; and trifluoromethyl;

wherein at least one protecting group is present on $R^{10}$ or $R^{11}$, or on a substituent on $A^1$.

* * * * *